United States Patent
Mizuguchi et al.

(10) Patent No.: US 12,075,839 B2
(45) Date of Patent: Sep. 3, 2024

(54) METHOD AND PROGRAM FOR OPERATING AN AEROSOL GENERATING DEVICE BY EARLY DETERMINATION OF AN AMOUNT OF AN AEROSOL SOURCE

(71) Applicant: JAPAN TOBACCO INC., Tokyo (JP)

(72) Inventors: Kazuma Mizuguchi, Tokyo (JP); Takeshi Akao, Tokyo (JP); Takuma Nakano, Tokyo (JP); Masayuki Tsuji, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 800 days.

(21) Appl. No.: 17/161,710

(22) Filed: Jan. 29, 2021

(65) Prior Publication Data
US 2021/0145069 A1   May 20, 2021

Related U.S. Application Data

(63) Continuation of application No. PCT/JP2018/028367, filed on Jul. 30, 2018.

(51) Int. Cl.
*A24F 40/53*     (2020.01)
*A24F 40/42*     (2020.01)
(Continued)

(52) U.S. Cl.
CPC .............. *A24F 40/53* (2020.01); *A24F 40/42* (2020.01); *A24F 40/57* (2020.01); *A61M 11/041* (2013.01);
(Continued)

(58) Field of Classification Search
CPC .......... A24F 40/53; A24F 40/57; A24F 40/42; A61M 11/041; A61M 15/06; G05B 15/02
See application file for complete search history.

(56) References Cited

U.S. PATENT DOCUMENTS

2011/0265806 A1* 11/2011 Alarcon ................ A24F 40/485
                                                        131/273
2013/0319435 A1* 12/2013 Flick .................... A61M 11/041
                                                        219/490
(Continued)

FOREIGN PATENT DOCUMENTS

EP       2 468 117 A1      6/2012
JP     2014-501105 A       1/2014
(Continued)

OTHER PUBLICATIONS

Extended European Search Report issued Jul. 1, 2021 in European Application No. 18928750.1.
(Continued)

*Primary Examiner* — Hae Moon Hyeon
(74) *Attorney, Agent, or Firm* — XSENSUS LLP

(57) ABSTRACT

An aerosol generating device which can infer or detect the state of at least one of a storage and a receptacle for an aerosol source, the aerosol generation device includes: a load which atomizes the aerosol source by generating heat with power supplied from a power source; a sensor which outputs values relating to the temperature of the load; and a controller. The controller infers or detects the state of at least one of the storage and the receptacle based on at least an output value of the sensor in a first power supply cycle, an output value of the sensor in a second power supply cycle, or a value relating to behavior of the temperature of the load in the second power supply cycle.

20 Claims, 22 Drawing Sheets

(51) Int. Cl.
  *A24F 40/57* (2020.01)
  *A61M 11/04* (2006.01)
  *A61M 15/06* (2006.01)
  *G05B 15/02* (2006.01)
(52) U.S. Cl.
  CPC .............. *A61M 15/06* (2013.01); *G05B 15/02* (2013.01); *A61M 2205/3368* (2013.01); *A61M 2205/52* (2013.01)

(56) References Cited

U.S. PATENT DOCUMENTS

| | | | |
|---|---|---|---|
| 2014/0020693 A1 | 1/2014 | Cochand et al. | |
| 2014/0299141 A1 | 10/2014 | Flick | |
| 2017/0035110 A1 | 2/2017 | Keen | |
| 2017/0251725 A1 | 9/2017 | Buchberger et al. | |
| 2018/0020735 A1 | 1/2018 | Bilat et al. | |
| 2020/0237015 A1* | 7/2020 | Yamada | H01M 10/48 |

FOREIGN PATENT DOCUMENTS

| | | |
|---|---|---|
| JP | 2014-530632 A | 11/2014 |
| JP | 2018-514191 A | 6/2018 |
| WO | 2012/085203 A1 | 6/2012 |
| WO | 2016/150922 A2 | 9/2016 |
| WO | 2017/021550 A1 | 2/2017 |
| WO | 2017/024477 A1 | 2/2017 |
| WO | 2017/084818 A1 | 5/2017 |
| WO | 2018/019533 A1 | 2/2018 |

OTHER PUBLICATIONS

Extended European Search Report issued Jun. 28, 2021 in European Application No. 18928752.7.
International Search Report and Written Opinion mailed on Sep. 18, 2018, received for PCT Application PCT/JP2018/028367, Filed on Jul. 30, 2018, 11 pages including English Translation.
International Search Report and Written Opinion mailed on Oct. 23, 2018, received for PCT Application PCT/JP2018/028365, Filed on Jul. 30, 2018, 11 pages including English Translation.
US Office Action issued Dec. 8, 2023, in related U.S. Appl. No. 17/161,661, 23 pages.
U.S. Office Action issued Mar. 18, 2024 in co-pending U.S. Appl. No. 17/161,661, 19 pages.

* cited by examiner

METHOD AND PROGRAM FOR OPERATING AN AEROSOL GENERATING DEVICE BY EARLY DETERMINATION OF AN AMOUNT OF AN AEROSOL SOURCE

CROSS REFERENCE TO RELATED APPLICATION

The present application is a continuation application of International Application No. PCT/JP2018/028367, filed on Jul. 30, 2018, the contents of which are incorporated by reference herein in its entirety.

TECHNICAL FIELD

The present disclosure relates to an aerosol generating device for generating aerosol inhaled by a user, and a method and a program for operating the aerosol generating device.

BACKGROUND ART

In an aerosol generating device for generating aerosol inhaled by a user, such as a conventional electronic cigarette, a heated tobacco product, a nebulizer or the like, if an inhalation action is performed by a user when there is a shortage of the quantity of an aerosol source which is to be atomized to become aerosol, a sufficient quantity of aerosol cannot be supplied to the user. Further, in the case of an electronic cigarette or a heated tobacco product, there will be a problem that aerosol having intended fragrance inhaling taste cannot be generated.

As a solution to the above problem, Patent Literature 1 discloses a technique to determine an empty state of an aerosol forming substrate, based on a threshold value and speed of raising of heater temperature in an early stage of an electric power supplying process. Patent Literature 2 discloses a technique to determine an empty state of an aerosol forming substrate, based on heater temperature at a point in time after a predetermined period of time has elapsed since a start of supply of electric power, or speed of raising of heater temperature in an early stage of an electric power supplying process. Patent Literature 3 discloses a technique to detect the quantity of liquid remaining in a wick, based on a resistance value of the wick.

In this regard, in the technique disclosed in Patent Literature 1 or 2, a minute quantity is focused on, and the threshold value must be set in such a manner that it is not affected by noise, errors, and so on, so that speed of judgment may become slow. Further, Patent Literature 3 does not disclose or suggest a method for speeding up judgment of an empty state of the remaining quantity of liquid in the wick.

Further, none of Patent Literatures 1-3 discloses or suggests, for example, a problem of estimating or detecting, so as to make it possible to distinguish in which portion of a tank for an aerosol forming substrate, a wick, and a path from the tank to the wick a problem such as a shortage of an aerosol source or the like has been occurring, at least one of a state of the tank and a state of the wick.

CITATION LIST

Patent Literature

PTL 1: PCT international publication No. WO 2012/085203
PTL 2: PCT international publication No. WO 2017/084818
PTL 3: PCT international publication No. WO 2017/021550

SUMMARY OF INVENTION

Technical Problem

The present disclosure has been made in view of the above matters.

A first problem to be solved by the present disclosure is to provide an aerosol generating device and a method and a program for operating the aerosol generating device by which occurrence of depletion or shortage of an aerosol source can be determined earlier.

A second problem to be solved by the present disclosure is to provide an aerosol generating device and a method and a program for operating the aerosol generating device by which a state of at least one of a storage unit and a holding unit for an aerosol source can be estimated or detected.

Solution to Problem

For solving the above first problem, according to an embodiment of the present disclosure, an aerosol generating device is provided, and the aerosol generating device comprising: a storage unit for storing an aerosol source or an aerosol base material for holding the aerosol source; a load for atomizing the aerosol source by heat generated by receiving supply of electric power from an electric power source; a sensor for outputting a value relating to temperature of the load; and a control unit, wherein the control unit is configured to: perform, in response to a request for generation of aerosol, electric power supplying cycles by supplying electric power from the electric power source to the load; and determine, based on an index derived based on a deviation of output values of the sensor obtained in a single one of the electric power supplying cycles, occurrence of depletion or shortage of the aerosol source in the storage unit or the aerosol base material.

According to the above embodiment, since depletion or shortage of the aerosol source can be determined based on a standard deviation, variance, or the like of the temperature of the load in a single electric power supplying cycle, occurrence of depletion or shortage of the aerosol source can be detected in an earlier stage.

In an embodiment, the control unit is configured to: determine occurrence of the depletion or the shortage, based on comparison between the index and an index derived based on a deviation of output values of the sensor obtained in a single one of the electric power supplying cycles when the depletion or the shortage has not been occurred.

According to the above embodiment, since a standard deviation, variance, or the like of the temperature of the load at the time of occurrence of depletion or shortage of the aerosol source can be used as a threshold value, occurrence of depletion or shortage of the aerosol source can be detected precisely.

In an embodiment, the control unit is configured to: eliminate or reduce effect of output values of the sensor on deriving the index, wherein the output values of the sensor are obtained at or during at least one of: the time of a start of a single one of the electric power supplying cycles, the time of an end of a single one of the electric power supplying cycles, one or more points in time in a single one of the electric power supplying cycles, and a period of time in a single one of the electric power supplying cycles. In an embodiment, the control unit is configured not to: obtain temperature of the load at or during at least one of: the time of a start of a single one of the electric power supplying cycles, the time of an end of a single one of the electric power supplying cycles, one or more points in time in a single one of the electric power supplying cycles, and a period of time in a single one of the electric power supplying cycles.

According to the above embodiments, since data including noise due to change in room temperature and so on can be excluded from data used for obtaining a standard deviation, variance, or the like of the temperature of the load, fluctuation of temperature at the time of occurrence of depletion or of the aerosol source is not hidden by the noise, so that precision of detection relating to depletion or occurrence of the aerosol source can be improved.

In an embodiment, the control unit is configured to: eliminate or reduce effect of output values of the sensor on deriving the index, wherein the output values are obtained in a warming period and/or a cooling period in a single one of the electric power supplying cycles.

In an embodiment, the control unit is configured not to: obtain temperature of the load in a warming period and/or a cooling period in a single one of the electric power supplying cycles.

According to the above embodiments, since data in the warming period and the cooling period can be excluded from data used for obtaining a standard deviation, variance, or the like, fluctuation of temperature at the time of occurrence of depletion or shortage of the aerosol source is not hidden by temperature change in the warming period and the cooling period, so that precision of detection relating to occurrence of depletion or shortage of the aerosol source can be improved.

In an embodiment, the control unit is configured to: divide a single one of the electric power supplying cycles into a plurality of phases that include a first phase and a second phase appearing after the first phase in a time series; and determine occurrence of the depletion or the shortage based on the index derived only from output values of the sensor obtained in the second phase.

In an embodiment, the control unit is configured to: divide a single one of the electric power supplying cycles into a plurality of phases that include a first phase and a second phase appearing after the first phase in a time series; and make effect of output values of the sensor obtained in the first phase on deriving the index lower than effect of output values of the sensor obtained in the second phase on deriving the index.

According to the above embodiments, since depletion or shortage of the aerosol source can be determined by using a standard deviation, variance, or the like that is based only on a latter part of samples obtained in the electric power supplying cycle, exceptional temperature fluctuation in a first part of the electric power supplying cycle, that occurs in the case that an excessive quantity of the aerosol source exists in the holding unit or the like, is less susceptible to be sensed, so that precision of detection relating to depletion or shortage of the aerosol source can be improved.

In an embodiment, the control unit is configured to: divide a single one of the electric power supplying cycles into a plurality of phases that include a first phase and a second phase appearing after the first phase in a time series; derive a first index that is the index derived from output values of the sensor obtained in the first phase and a second index that is the index derived from output values of the sensor obtained in the second phase; and determine occurrence of the depletion or the shortage based on a difference between the second index and the first index.

According to the above embodiments, since depletion or shortage of the aerosol source can be determined by using a difference between standard deviations, values of variance, or the like obtained in a first part and a latter part in the data obtained in the electric power supplying cycle, temperature fluctuation in the latter part of the electric power supplying cycle, that occurs only when the aerosol source is depleted in the holding unit, is emphasized, so that precision of detection relating to depletion or shortage of the aerosol source can be improved.

In an embodiment, the first phase is shorter than the second phase.

According to the above embodiments, since the data obtained in the electric power supplying cycle can be divided in such a manner that a latter part of the data becomes long, a part that does not include temperature fluctuation in the electric power supplying cycle can be excluded, so that precision of detection relating to occurrence of depletion or shortage of the aerosol source can be improved.

In an embodiment, the control unit is configured to: determine occurrence of the depletion or the shortage based on the index that is derived from at least part of output values of the sensor that are obtained after the output values of the sensor have reached a steady state.

According to the above embodiments, depletion or shortage of the aerosol source can be determined by using a standard deviation, variance, or the like of the temperature of the load that is focused on fluctuation of temperature that may occur after the temperature of the load enters a steady state, so that precision of detection relating to depletion or shortage of the aerosol source can be improved.

In an embodiment, the control unit is configured to: divide a single one of the electric power supplying cycles into a plurality of phases that include a first phase and a second phase appearing after the first phase in a time series; and determine whether the output values of the sensor have reached a steady state based on at least one of: the index derived from the output values of the sensor obtained in the first phase, the output values of the sensor obtained in the first phase, and an average value of the output values of the sensor obtained in the first phase.

According to the above embodiments, whether the temperature of the load has entered a steady state is determined based on an average value, a standard deviation, variance, or the like of the temperature of the load, it becomes possible to determine whether the temperature of the load has entered a steady state by using a simple method that does not require a dedicated sensor, a dedicated algorithm, or the like.

In an embodiment, the control unit is configured to determine occurrence of the depletion or the shortage based on: the index; and output values of the sensor or an average value of the output values of the sensor obtained in a single one of the electric power supplying cycles.

According to the above embodiments, depletion or shortage of the aerosol source can be determined by using average temperature along with a standard deviation, variance, or the like of the temperature of the load, so that precision of detection relating to depletion or shortage of the aerosol source can be improved.

In an embodiment, the control unit is configured to: detect occurrence of the depletion or the shortage only when output values of the sensor or an average value of the output values of the sensor obtained in a single one of the electric power supplying cycles are/is higher than temperature at which aerosol is generated from the aerosol source.

According to the above embodiments, since depletion or shortage of the aerosol source can be detected only when average temperature of the load exceeds a boiling point of the aerosol source or the like, exceptional temperature fluctuation is less susceptible to be sensed, so that precision of detection relating to depletion or shortage of the aerosol source can be improved.

Further, according to an embodiment of the present disclosure, a method for operating an aerosol generating device is provided, wherein the aerosol generating device comprises: a storage unit for storing an aerosol source or an aerosol base material for holding the aerosol source; a load for atomizing the aerosol source by heat generated by receiving supply of electric power from an electric power source; a sensor for outputting a value relating to temperature of the load; and a control unit, wherein the method comprises steps of, by the control unit: performing, in response to a request for generation of aerosol, electric power supplying cycles by supplying electric power from the electric power source to the load; and determining, based on an index derived based on a deviation of output values of the sensor obtained in a single one of the electric power supplying cycles, occurrence of depletion or shortage of the aerosol source in the storage unit or the aerosol base material.

According to an embodiment of the present disclosure, an aerosol generating device is provided, and the aerosol generating device comprising: a storage unit for storing an aerosol source or an aerosol base material for holding the aerosol source; a load for atomizing the aerosol source by heat generated by receiving supply of electric power from an electric power source; a sensor for outputting a value relating to temperature of the load; and a control unit, wherein the control unit is configured to: perform, in response to a request for generation of aerosol, electric power supplying cycles by supplying electric power from the electric power source to the load; and determine, based on behavior of output values of the sensor obtained after the output values of the sensor have reached a steady state in a single one of the electric power supplying cycles, occurrence of depletion or shortage of the aerosol source in the storage unit or the aerosol base material. According to an embodiment of the present disclosure, a method for operating an aerosol generating device is provided, wherein the aerosol generating device comprises: a storage unit for storing an aerosol source or an aerosol base material for holding the aerosol source; a load for atomizing the aerosol source by heat generated by receiving supply of electric power from an electric power source; a sensor for outputting a value relating to temperature of the load; and a control unit, wherein the method comprises steps of, by the control unit: performing, in response to a request for generation of aerosol, electric power supplying cycles by supplying electric power from the electric power source to the load; and determining, based on behavior of output values of the sensor obtained after the output values of the sensor have reached a steady state in a single one of the electric power supplying cycles, occurrence of depletion or shortage of the aerosol source in the storage unit or the aerosol base material.

According to embodiments of the present disclosure, programs are provided, and the programs cause a processor to perform the above methods, when the programs are executed by the processor.

According to the above embodiment, since depletion or shortage of the aerosol source can be determined based on a standard deviation, variance, or the like of the temperature of the load in a single electric power supplying cycle, occurrence of depletion or shortage of the aerosol source can be detected in an earlier stage.

For solving the above second problem, according to an embodiment of the present disclosure, an aerosol generating device is provided, and the aerosol generating device comprising: a storage unit for storing an aerosol source; a load for atomizing the aerosol source by heat generated by receiving supply of electric power from an electric power source; a holding unit for holding the aerosol source, which is supplied from the storage unit, in a state that the aerosol source can be heated by the load; a sensor for outputting a value relating to temperature of the load; and a control unit, wherein the control unit is configured to: perform, in response to a request for generation of aerosol, electric power supplying cycles by supplying electric power from the electric power source to the load; and estimate or detect at least one of a state of the storage unit and a state of the holding unit based at least on first values and second values, and wherein the first values are: output values of the sensor obtained in a first electric power supplying cycle, or values relating to behavior of the temperature of the load in the first electric power supplying cycle, the values derived from the output values obtained in the first electric power supplying cycle; the first electric power supplying cycle is a single one of the electric power supplying cycles; the second values are: output values of the sensor obtained in a second electric power supplying cycle, or values relating to behavior of the temperature of the load in the second electric power supplying cycle, the values derived from the output values obtained in the second electric power supplying cycle; and the second electric power supplying cycle is a single one of the electric power supplying cycles occurring after the first electric power supplying cycle.

According to the above embodiment, since the states of the storage unit and the holding unit can be estimated based on behavior of the temperature of the load in the past and the present, the states of the storage unit and the holding unit can be determined in an earlier stage and precisely.

In an embodiment, the control unit is configured to: estimate or detect, in case that at least one the first values and the second values represent that the temperature of the load has reached a steady state at second temperature that is higher than first temperature at which aerosol is generated from the holding unit in a saturation state of the aerosol source, at least one of: a remaining quantity of the aerosol source in the storage unit, a remaining quantity of the aerosol source in the holding unit, and relationship between speed of atomization of the aerosol source in the holding unit and speed of supply of the aerosol source from the storage unit to the holding unit.

According to the above embodiment, since it is possible to detect an event that the temperature of the load in an electric power supplying cycle in the past or the present became or has become stable at temperature higher than a boiling point of the aerosol source or the like, it becomes possible to identify a state that a problem has been occurring in any of the storage unit, the holding unit, and a part between the storage unit and the holding unit.

In an embodiment, the control unit is configured to: estimate or detect, in a case that the first values represent that the temperature of the load has reached a steady state at the second temperature, at least one of: shortage or depletion of a remaining quantity of the aerosol source in the storage unit, and that speed of atomization of the aerosol source in the holding unit is faster than speed of supply of the aerosol source from the storage unit to the holding unit.

According to the above embodiment, since it is possible to detect an event that the temperature of the load in an electric power supplying cycle in the past became stable at temperature higher than a boiling point of the aerosol source or the like, it becomes possible to identify a state that a problem has been occurring in the storage unit or a part between the storage unit and the holding unit.

In an embodiment, the control unit is configured to: estimate or detect, in a case that the first values represent that the temperature of the load has reached a steady state at the second temperature, and that the second values represent that the temperature of the load has reached a steady state at the second temperature, shortage or depletion of a remaining quantity of the aerosol source in the storage unit.

According to the above embodiment, since it is possible to detect events that the temperature of the load in electric power supplying cycles in the past and the present became and has become stable at temperature higher than a boiling point of the aerosol source or the like, it becomes possible to identify a state that a problem has been occurring in the storage unit.

In an embodiment, the control unit is configured to: estimate or detect, in a case that the first values represent that the temperature of the load has reached a steady state at the second temperature, and that the second values represent that the temperature of the load has reached a steady state at the first temperature, that speed of atomization of the aerosol source in the holding unit is faster than speed of supply of the aerosol source from the storage unit to the holding unit.

According to the above embodiment, since it is possible to detect an event that the temperature of the load in a past electric power supplying cycle became stable at temperature higher than a boiling point of the aerosol source or the like, and the temperature of the load in a present electric power supplying cycle has become stable at the boiling point of the aerosol source or the like, it becomes possible to identify a state that a problem has been occurring in a part between the storage unit and the holding unit.

In an embodiment, the control unit is configured to estimate or detect, in a case that the second values represent that the temperature of the load has reached a steady state at the second temperature, that shortage or depletion of a remaining quantity of the aerosol source in the storage unit has been occurring.

According to the above embodiment, since it is possible to detect an event that the temperature of the load in a present electric power supplying cycle has become stable at temperature higher than a boiling point of the aerosol source or the like, it becomes possible to identify a state that a problem has been occurring in the storage unit.

In an embodiment, the control unit is configured to estimate or detect, in a case that the first values represent that the temperature of the load has reached a steady state at the second temperature, and that at least one of an average value of the second value and a value derived based on deviation of the second value is greater than a threshold value: that shortage or depletion of a remaining quantity of the aerosol source in the storage unit has been occurring, and that depletion of a remaining quantity of the aerosol source in the holding unit has been occurring.

According to the above embodiment, since it is possible to detect an event that the temperature of the load in a past electric power supplying cycle became stable at temperature higher than a boiling point of the aerosol source or the like, and the temperature of the load in a present electric power supplying cycle is fluctuating roughly, it becomes possible to detect depletion of a remaining quantity of the aerosol source in the holding unit.

In an embodiment, the control unit is configured to estimate or detect, in a case that the second values represent that the temperature of the load has reached a steady state at temperature higher than temperature at which aerosol is generated from the holding unit in a saturation state of the aerosol source, that a remaining quantity of the aerosol source in the holding unit will be depleted after completion of a predetermined number of times of the electric power supplying cycles.

According to the above embodiment, since it is possible to detect an event that the temperature of the load in a present electric power supplying cycle becomes stable at temperature higher than a boiling point of the aerosol source or the like, it becomes possible to detect a symptom of depletion of the aerosol source in the holding unit.

In an embodiment, the control unit is configured to estimate or detect, in a case that both the first values and the second values represent that the temperature of the load has reached a steady state at temperature higher than temperature at which aerosol is generated from the aerosol source, that a remaining quantity of the aerosol source in the holding unit will be depleted after completion of a predetermined number of times of the electric power supplying cycles.

According to the above embodiment, since it is possible to detect an event that the temperature of the load in electric power supplying cycles in the past and in the present became and has become stable at temperature higher than a boiling point of the aerosol source or the like, it becomes possible to detect a symptom of depletion of the aerosol source in the holding unit.

In an embodiment, the control unit is configured to determine, based on at least one of: continuous output values of the sensor in the first electric power supplying cycle or the second electric power supplying cycle, an average value of the output values in the first electric power supplying cycle or the second electric power supplying cycle, and a value derived based on deviation of the output values in the first electric power supplying cycle or the second electric power supplying cycle, that the first values or the second values represent that the temperature of the load has reached a steady state.

According to the above embodiment, whether the temperature of the load has been entered a steady state is determined based on an average value of the temperature of the load, a standard deviation, variance, or the like in a first part of an electric power supplying cycle, it becomes possible to determine whether the temperature of the load has been entered a steady state, by using a simple method that does not require a dedicated sensor, a dedicated algorithm, or the like.

Further, according to an embodiment of the present disclosure, a method for operating an aerosol generating device is provided, wherein the aerosol generating device comprises: a storage unit for storing an aerosol source; a load for atomizing the aerosol source by heat generated by receiving supply of electric power from an electric power source; a holding unit for holding the aerosol source, which is supplied from the storage unit, in a state that the aerosol source can be heated by the load; a sensor for outputting a value relating to temperature of the load; and a control unit; and wherein the method comprises steps of, by the control unit: performing, in response to a request for generation of aerosol, electric power supplying cycles by supplying electric power from the electric power source to the load; and estimating or detecting at least one of a state of the storage unit and a state of the holding unit based at least on first values and second values, and wherein the first values are: output values of the sensor obtained in a first electric power supplying cycle, or values relating to behavior of the temperature of the load in the first electric power supplying cycle, the values derived from the output values obtained in the first electric power supplying cycle; the first electric power supplying cycle is a single one of the electric power supplying cycles; the second values are: output values of the sensor obtained in a second electric power supplying cycle, or values relating to behavior of the temperature of the load in the second electric power supplying cycle, the values derived from the output values obtained in the second electric power supplying cycle; and the second electric power supplying cycle is a single one of the electric power supplying cycles occurring after the first electric power supplying cycle.

According to an embodiment of the present disclosure, an aerosol generating device is provided, and the aerosol generating device comprising: a storage unit for storing an aerosol source; a load for atomizing the aerosol source by heat generated by receiving supply of electric power from an electric power source; a holding unit for holding the aerosol source, which is supplied from the storage unit, in a state that the aerosol source can be heated by the load; a sensor for outputting a value relating to temperature of the load; and a control unit, wherein the control unit is configured to: perform, in response to a request for generation of aerosol, electric power supplying cycles by supplying electric power from the electric power source to the load; derive, based on output values of the sensor, temperature of the load in a single one of the electric power supplying cycles; and estimate or detect, in a case that the temperature of the load has been in a steady state at temperature in a plurality of the electric power supplying cycles, the temperature being higher than temperature at which aerosol is generated from the holding unit in a saturation state of the aerosol source: that shortage or depletion of a remaining quantity of the aerosol source in the storage unit has been occurring, or that a remaining quantity of the aerosol source in the holding unit will be depleted after completion of a predetermined number of times of the electric power supplying cycles.

According to an embodiment of the present disclosure, a method for operating an aerosol generating device is provided, wherein the aerosol generating device comprises: a storage unit for storing an aerosol source; a load for atomizing the aerosol source by heat generated by receiving supply of electric power from an electric power source; a holding unit for holding the aerosol source, which is supplied from the storage unit, in a state that the aerosol source can be heated by the load; a sensor for outputting a value relating to temperature of the load; and a control unit, and wherein the method comprises steps of, by the control unit: performing, in response to a request for generation of aerosol, electric power supplying cycles by supplying electric power from the electric power source to the load; deriving, based on output values of the sensor, temperature of the load in a single one of the electric power supplying cycles; and estimating or detecting, in a case that the temperature of the load has been in a steady state at temperature in a plurality of the electric power supplying cycles, the temperature being higher than temperature at which aerosol is generated from the holding unit in a saturation state of the aerosol source: that shortage or depletion of a remaining quantity of the aerosol source in the storage unit has been occurring, or that a remaining quantity of the aerosol source in the holding unit will be depleted after completion of a predetermined number of times of the electric power supplying cycles.

According to an embodiment of the present disclosure, an aerosol generating device is provided, and the aerosol generating device comprising: a storage unit for storing an aerosol source; a load for atomizing the aerosol source by heat generated by receiving supply of electric power from an electric power source; a holding unit for holding the aerosol source, which is supplied from the storage unit, in a state that the aerosol source can be heated by the load; a sensor for outputting a state of the load or the storage unit; and a control unit, wherein the control unit is configured to: in a case that output values of the sensor represents shortage or depletion of a remaining quantity of the aerosol source in the storage unit but do not represent depletion of a remaining quantity of the aerosol source in the holding unit, estimate or detect that a remaining quantity of the aerosol source in the holding unit will be depleted after completion of a predetermined number of times of the electric power supplying cycles, or suppress supply of electric power to the load after completion of a predetermined number of times of the electric power supplying cycles.

According to an embodiment of the present disclosure, a method for operating an aerosol generating device is provided, wherein the aerosol generating device comprises: a storage unit for storing an aerosol source; a load for atomizing the aerosol source by heat generated by receiving supply of electric power from an electric power source; a holding unit for holding the aerosol source, which is supplied from the storage unit, in a state that the aerosol source can be heated by the load; a sensor for outputting a state of the load or the storage unit; and a control unit, and wherein the method comprises a step of, by the control unit: in a case that output values of the sensor represents shortage or depletion of a remaining quantity of the aerosol source in the storage unit but do not represent depletion of a remaining quantity of the aerosol source in the holding unit, estimating or detecting that a remaining quantity of the aerosol source in the holding unit will be depleted after completion of a predetermined number of times of the electric power supplying cycles, or suppressing supply of electric power to the load after completion of a predetermined number of times of the electric power supplying cycles.

According to embodiments of the present disclosure, programs are provided, and the programs cause a processor to perform the above methods, when the programs are executed by the processor.

According to the above embodiments, since the states of the storage unit and the holding unit can be estimated based on behavior of the temperature of the load in the past and the present, the states of the storage unit and the holding unit can be determined in an earlier stage and precisely.

DESCRIPTION OF EMBODIMENTS

1 Outline of Aerosol Generating Device

Figure 1A:
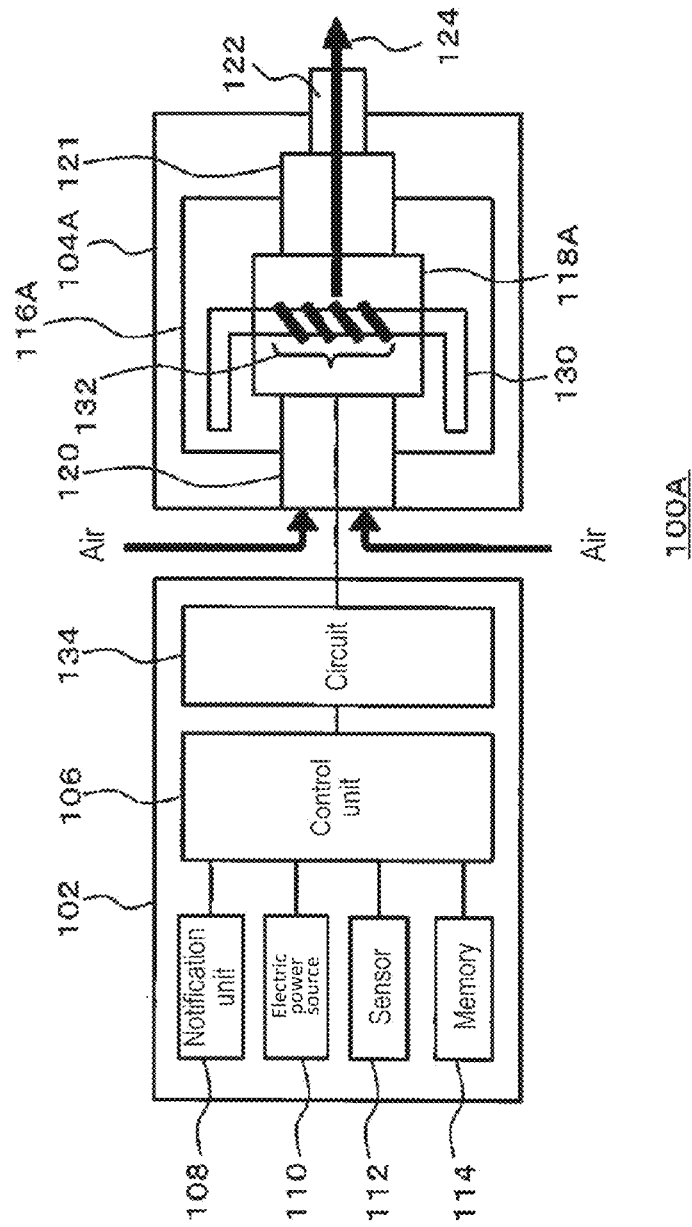
FIG. 1A is a schematic block diagram of a configuration of an aerosol generating device according to an embodiment of the present disclosure.

FIG. 1A is a schematic block diagram of a configuration of an aerosol generating device 100A according to an embodiment of the present disclosure. It should be reminded that FIG. 1A is that schematically and conceptually showing respective components included in the aerosol generating device 100A, and is not that showing precise arrangement, shapes, sizes, positional relationship, and so on of the respective components and the aerosol generating device 100A.

As shown in FIG. 1A, the aerosol generating device 100A comprises a first member 102 (hereinafter, this will be referred to as a "main body 102") and a second member 104A (hereinafter, this will be referred to as a "cartridge 104A"). As shown in the figure, in an example, the main body 102 may comprise a control unit 106, a notification unit 108, an electric power source 110, a sensor 112, and a memory 114. The aerosol generating device 100A may comprise sensors such as a flow rate sensor, a pressure sensor, a voltage sensor, a temperature sensor, and so on, and they are also collectively referred to as a "sensor 112" in this disclosure. The main body 102 may also comprise a circuit 134 which will be explained later. For example, the cartridge 104A may comprise a storage unit 116A, an atomization unit 118A, an air taking-in flow path 120, an aerosol flow path 121, a suction opening 122, a holding unit 130, and a load 132. Part of components included in the main body 102 may be included in the cartridge 104A. Part of components included in the cartridge 104A may be included in the main body 102. The cartridge 104A may be configured to be attachable/detachable to/from the main body 102. Alternatively, all components included in the main body 102 and cartridge 104A may be included in a single housing in place of the main body 102 and the cartridge 104A.

The storage unit 116A may be configured as a tank for storing an aerosol source. In the above case, the aerosol source is liquid such as polyhydric alcohol, such as glycerin or propylene glycol, or water, or the like, for example. In the case that the aerosol generating device 100A is an electronic cigarette, the aerosol source may comprise a tobacco raw material or an extract originated from a tobacco raw material, which releases a fragrance-inhaling-taste component when it is heated. The holding unit 130 holds the aerosol source. For example, the holding unit 130 comprises fibrous or porous material, and holds the aerosol source, which is in the form of liquid, by use of spaces between fibers or pores in the porous material. For example, cotton or glass fibers, or tobacco raw material, or the like may be used as the above-explained fibrous or porous material. In the case that the aerosol generating device 100A is an inhaler for medical use, such as a nebulizer or the like, the aerosol source may comprise a medicine that is to be inhaled by a patient. In a different example, the storage unit 116A may have a configuration which allows replenishment of a consumed aerosol source. Alternatively, the storage unit 116A may be configured in such a manner that the storage unit 116A itself is allowed to be replaced when the aerosol source is exhausted. Further, the aerosol source is not limited to that in a liquid form, and it may be solid. The storage unit 116A may be a hollow container, in the case that the aerosol source is solid.

The atomization unit 118A is configured to atomize an aerosol source to generate aerosol. When an inhalation action is detected by the sensor 112, the atomization unit 118A generates aerosol. For example, the holding unit 130 is arranged to connect the storage unit 116A and the atomization unit 118A. In the above case, a part of the holding unit 130 enters the inside of the storage unit 116A to bring it in contact with the aerosol source. The other part of the holding unit 130 extends toward the atomization unit 118A. It should be reminded that the other part of the holding unit 130 extending toward the atomization unit 118A may be held in the atomization unit 118A, or extended through the atomization unit 118A to enter the inside of the storage unit 116A again. The aerosol source is conveyed from the storage unit 116A to the atomization unit 118A by the capillary effect in the holding unit 130. For example, the atomization unit 118A comprises a heater which comprises a load 132 which is electrically connected to the electric power source 110. The heater is arranged in such a manner that it is in contact with or is positioned close to the holding unit 130. When an inhalation action is detected, the control unit 106 controls the heater in the atomization unit 118A to atomize an aerosol source, which is conveyed via the holding unit 130, by heating the aerosol source. The air taking-in flow path 120 is connected to the atomization unit 118A, and the air taking-in flow path 120 leads to the outside of the aerosol generating device 110A. The aerosol generated in the atomization unit 118A is mixed with air, which is taken via the air taking-in flow path 120. The fluid mixture comprising the aerosol and the air is sent to the aerosol flow path 121, as shown by an arrow 124. The aerosol flow path 121 has a tubular structure for sending the fluid mixture comprising the air and the aerosol, that is generated in the atomization unit 118A, to the suction opening 122.

The suction opening 122 is configured in such a manner that it is positioned at an end of the aerosol flow path 121, and is opened to the outside of the aerosol generating device 100A. A user takes air including the aerosol into the mouth by holding the suction opening 122 in the user's mouth and inhaling the air.

The notification unit 108 may comprise a light emitting element such as a light-emitting diode (LED), a display, a speaker, a vibrator, and so on. The notification unit 108 is configured to provide a user with some information by light emission, display, vocalization, vibration, or the like, as necessary.

The electric power source 110 supplies electric power to the respective components in the aerosol generating device 100A, such as the notification unit 108, the sensor 112, the memory 114, the load 132, the circuit 134, and so on. The electric power source 110 may be a primary battery or a secondary battery which can be charged by connecting it to an external electric power source via a predetermined port (not shown in the figure) of the aerosol generating device 100A. The electric power source 110 only may be able to be detached from the main body 102 or the aerosol generating device 100A, and may be able to be replaced by a new electric power source 110. Further, the electric power source 110 may be able to be replaced by a new electric power source 110, by replacing the whole main body 102 by a new main body 102.

The sensor 112 may comprise one or more sensors used for obtaining a value of a voltage applied to the whole part or a specific part of the circuit 134, a value relating to a resistance value of the load 132, or a value relating to temperature, or the like. The sensor 112 may be incorporated in the circuit 134. The function of the sensor 112 may be incorporated in the control unit 106. The sensor may also comprise a pressure sensor for detecting change in the pressure in the air taking-in flow path 120 and/or the aerosol flow path 121, or a flow rate sensor for detecting a flow rate. Further, the sensor 112 may comprise a weight sensor for detecting the weight of a component such as the storage unit 116A or the like. Further, the sensor 112 may be configured to count the number of times of puffs performed by a user by using the aerosol generating device 100A. Further, the sensor 112 may be configured to accumulate time of electrical conduction to the atomization unit 118A. Further, the sensor 112 may be configured to detect height of a liquid surface in the storage unit 116A. Further, the sensor 112 may be configured to obtain or detect an SOC (State of Charge), an integrated current value, a voltage, or the like of the electric power source 110. The SOC may be obtained by using a current integration method (a coulomb count method), an SOC-OCV (Open Circuit Voltage) method, and so on. Further, the sensor 112 may be a manipulation button which can be manipulated by a user.

The control unit 106 may be an electronic circuit module configured as a microprocessor or a microcomputer. The control unit 106 may be configured to control operation of the aerosol generating device 100A in accordance with computer-executable instructions stored in the memory 114. The memory 114 is a storing medium such as a read-only memory (ROM), a random-access memory (RAM), a flash memory, or the like. The memory 114 may store, in addition to computer-executable instructions such as those explained above, setting data which are necessary for controlling the aerosol generating device 100A and other data. For example, the memory 114 may store various data such as methods for controlling the notification unit 108 (modes of light emission, vocalization, vibration, etc., and so on), values obtained and/or detected by the sensor 112, history of heat of the atomization unit 118A, and so on. The control unit 106 reads data from the memory 114 as necessary and uses the data for controlling the aerosol generating device 110A, and stores data in the memory 114 as necessary.

Figure 1B:
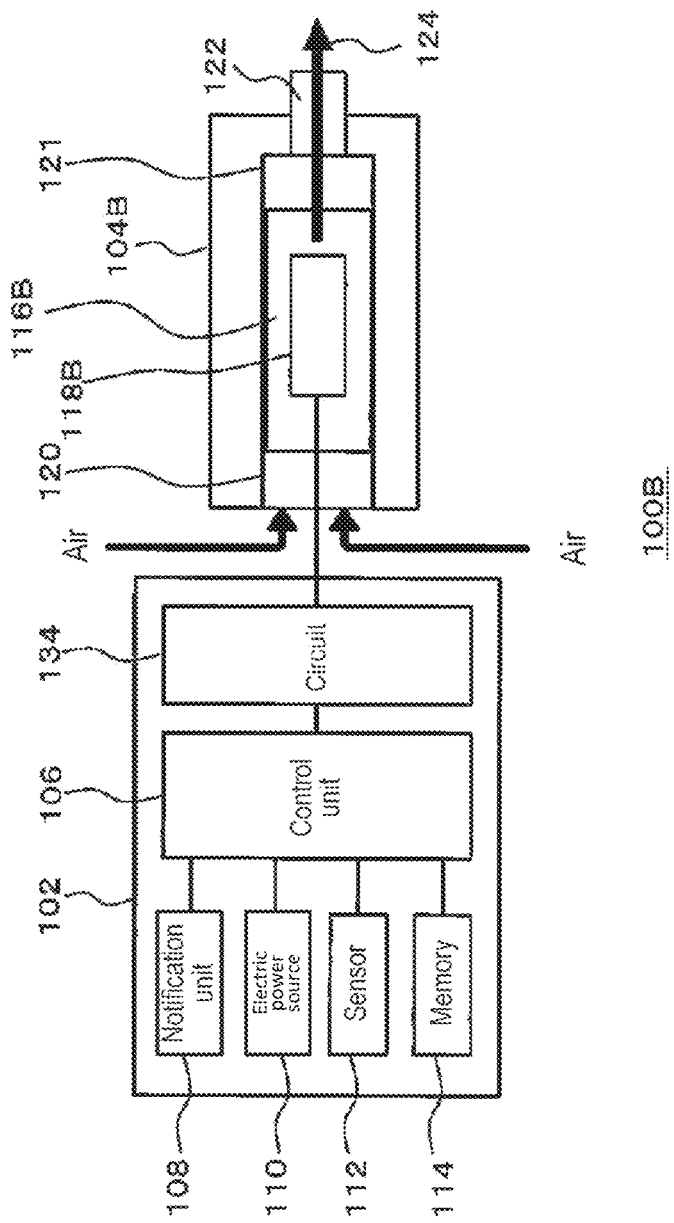
FIG. 1B is a schematic block diagram of a configuration of an aerosol generating device according to an embodiment of the present disclosure.

FIG. 1B is a schematic block diagram of a configuration of an aerosol generating device 100B according to an embodiment of the present disclosure.

As shown in the figure, the aerosol generating device 100B has a configuration similar to that of the aerosol generating device 100A in FIG. 1A. However, the configuration of a second member 104B (hereinafter, this will be referred to as an "aerosol generating article 104B" or a "stick 104B") is different from the configuration of the first member 104A. In an example, the aerosol generating article 104B may comprise an aerosol base material 116B, an atomization unit 118B, an air taking-in flow path 120, an aerosol flow path 121, and a suction opening 122. Part of components included in the main body 102 may be included in the aerosol generating article 104B. Part of components included in the aerosol generating article 104B may be included in the main body 102. The aerosol generating article 104B may be configured to be able to be inserted/extracted in/from the main body 102. Alternatively, all components included in the main body 102 and aerosol generating article 104B may be included in a single housing in place of the main body 102 and the aerosol generating article 104B.

The aerosol base material 116B may be configured as a solid which holds an aerosol source. Similar to the case of the storage unit 116A in FIG. 1A, the aerosol source may be liquid such as polyhydric alcohol, such as glycerin or propylene glycol, or water, or the like, for example. The aerosol source may comprise a tobacco raw material or an extract originated from a tobacco raw material, which releases a fragrance-inhaling-taste component when it is heated. In the case that the aerosol generating device 100B is an inhaler for medical use, such as a nebulizer or the like, the aerosol source may also comprise a medicine that is to be inhaled by a patient. The aerosol base material 116B may be configured in such a manner that the aerosol base material 116B itself is allowed to be replaced when the aerosol source is exhausted. Further, the aerosol source is not limited to that in a liquid form, and it may be solid.

The atomization unit 118B is configured to atomize an aerosol source to generate aerosol. When an inhalation action is detected by the sensor 112, the atomization unit 118B generates aerosol. The atomization unit 118B comprises a heater (which is not shown in the figure) which comprises a load electrically connected to the electric power source 110. When an inhalation action is detected, the control unit 106 controls the heater in the atomization unit 118B to atomize an aerosol source, which is held in the aerosol base material 116B, by heating the aerosol source. The air taking-in flow path 120 is connected to the atomization unit 118B, and the air taking-in flow path 120 leads to the outside of the aerosol generating device 110B. The aerosol generated in the atomization unit 118B is mixed with air, which is taken via the air taking-in flow path 120. The fluid mixture comprising the aerosol and the air is sent to the aerosol flow path 121, as shown by an arrow 124. The aerosol flow path 121 has a tubular structure for sending the fluid mixture comprising the air and the aerosol, that is generated in the atomization unit 118B, to the suction opening 122.

The control unit 106 is configured to control the aerosol generating devices 100A and 100B (hereinafter, they may be collectively referred to as an "aerosol generating device 100") relating to the embodiments of the present disclosure by use of various methods.

Figure 2:
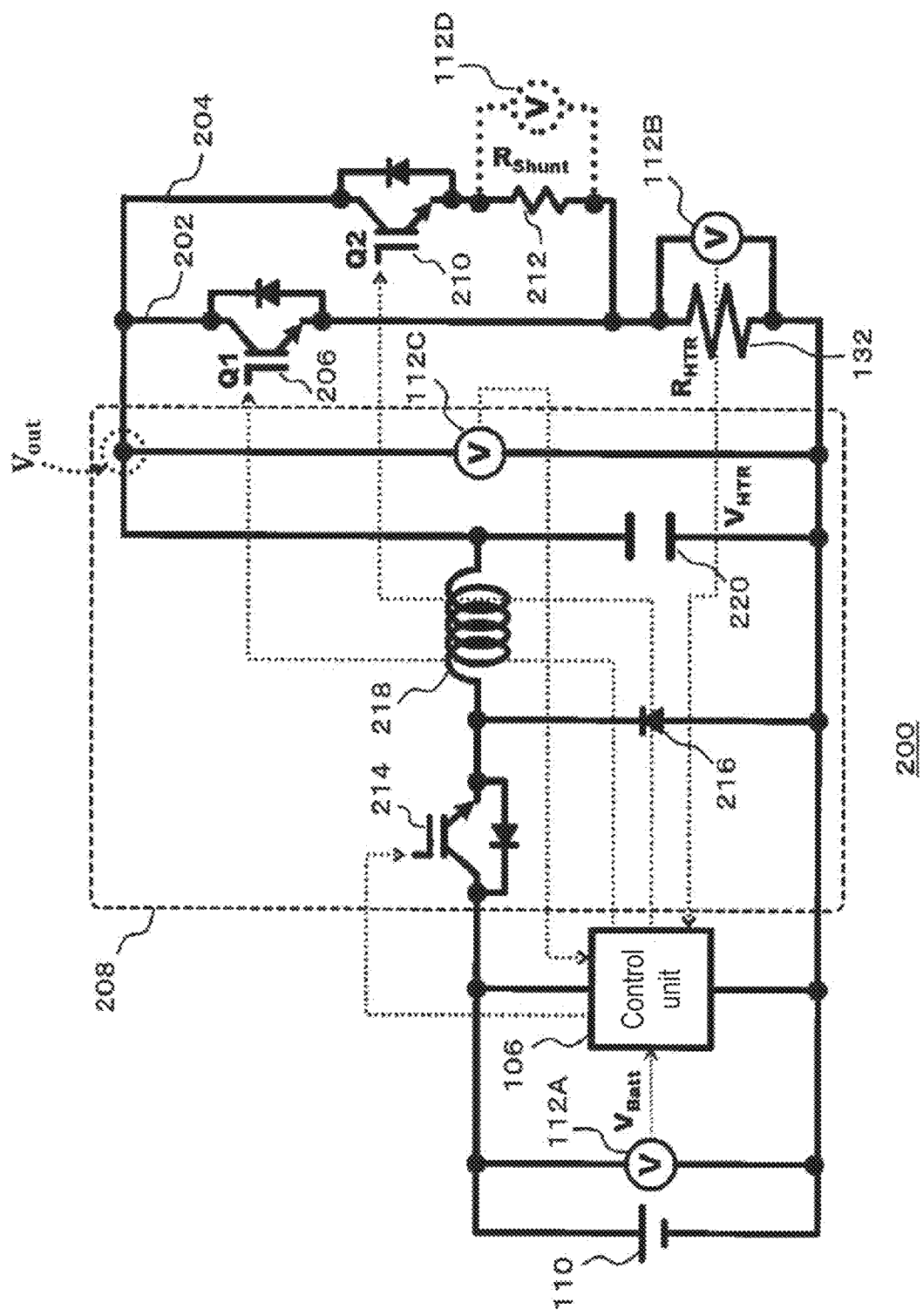
FIG. 2 is a figure showing an example circuit configuration relating to part of an aerosol generating device according to an embodiment of the present disclosure.

FIG. 2 is a figure showing an example circuit configuration relating to part of an aerosol generating device 100 according to an embodiment of the present disclosure.

A circuit 200 shown in FIG. 2 comprises an electric power source 110, a control unit 106, sensors 112A-D (hereinafter, they may be collectively referred to as a "sensor 112"), a load 132 (hereinafter, this may be referred to as a "heater resistance"), a first circuit switch 202, a second circuit switch 204, a switch Q1 comprising a first field effect transistor (FET) 206, a conversion unit 208, a switch Q2 comprising a second FET 210, and a resistance 212 (hereinafter, this may be referred to as a "shunt resistance"). The electric resistance value of the load 132 changes according to temperature. The shunt resistance 212 is connected to the load 132 in parallel, and has a known electric resistance value. The electric resistance value of the shunt resistance 212 may be unchanged in relation to temperature. The shunt resistance 212 has an electric resistance value greater than that of the load 132. Depending on an embodiment, the sensors 112C and 112D may be omitted. It will be obvious to a person skilled in the art that various elements such as an insulated-gate bipolar transistor (IGBT), a contactor, and so on, in addition to an FET, can be used as each of the switches Q1 and Q2. Further, although it is preferable that the switches Q1 and Q2 have the same characteristic, they may be those having different characteristics. Thus, although it is preferable that FETs, IGBTs, contactors, and so on used as the switches Q1 and Q2 have the same characteristic, they may be those having different characteristics.

The conversion unit 208 may be a switching converter, and may comprise an FET 214, a diode 216, an inductor 218, and a capacitor 220. The control unit 106 may control the conversion unit 208 in such a manner that the conversion unit 208 converts an output voltage of the electric power source 110 and the converted output voltage is applied to the whole circuit. In this regard, it is preferable that the conversion unit 208 be configured to be controlled by the control unit 106 to output a constant voltage during at least a period that the switch Q2 is in an ON state. Further, the conversion unit 208 may be configured to be controlled by the control unit 106 to output a constant voltage during a period that the switch Q1 is in an ON state also, or output a constant voltage always. It should be reminded that the constant voltage outputted from the conversion unit 208 controlled by the control unit 106 during the period that the switch Q1 is in an ON state and the constant voltage outputted from the conversion unit 208 controlled by the control unit 106 during the period that the switch Q2 is in an ON state may be the same with each other or different from each other. In the case that they are different from each other, the constant voltage outputted from the conversion unit 208 controlled by the control unit 106 during the period that the switch Q1 is in an ON state may be higher or lower than the constant voltage outputted from the conversion unit 208 controlled by the control unit 106 during the period that the switch Q2 is in an ON state. According to the above configuration, the voltage and a parameter at the time of measurement of the voltage become stable, so that precision of estimation of the remaining quantity of the aerosol source is improved. Further, the conversion unit 208 may be configured to be controlled by the control unit 106 in such a manner that the output voltage of the electric power source 110 is directly applied to the first circuit during a period that the switch Q1 only is in an ON state. It should be reminded that the conversion unit 208 is not an indispensable component, so that it may be omitted.

The circuit 134 shown in FIG. 1A electrically connects the electric power source 110 and the load 132, and may comprise the first circuit 202 and the second circuit 204. The first circuit 202 and the second circuit 204 are connected to the electric power source 110 and the load 132 in parallel. The first circuit 202 may comprise the switch Q1. The second circuit 204 may comprise the switch Q2 and the resistance 212 (and a sensor 112D, optionally). The first circuit 202 may have a resistance value smaller than that of the second circuit 204. In this example, the sensor 112B and 112D are voltage sensors, and are configured to detect voltage differences (hereinafter, they may be referred to as "voltages" or "voltage values") across the load 132 and the resistance 212, respectively. In this regard, the configuration of the sensor 112 is not limited to those explained above. For example, the sensor 112 may be a current sensor for detecting a value of current flowing through the load 132 and/or the resistance 212.

As shown in FIG. 2 by using dotted-line arrows, the control unit 106 can control the switch Q1, the switch Q2, and so on, and obtain values detected by the sensor 112. The control unit 106 may be configured to activate the first circuit 202 by switching the state of the switch Q1 from an OFF state to an ON state, and activate the second circuit 204 by switching the state of the switch Q2 from an OFF state to an ON state. The control unit 106 may be configured to alternatively activate the first circuit 202 and the second circuit 204 by alternatively switching the switch Q1 and the switch Q2.

The first circuit is used for atomization of the aerosol source. When the state of the switch Q1 is switched to an ON state and the first circuit 202 is activated, electric power is supplied to the heater (i.e., the load 132 in the heater) and the load 132 is heated. As a result that the load 132 is heated, the aerosol source held in the holding unit 130 in the atomization unit 118A (the aerosol source held in the aerosol base material 116B, in the case of the aerosol generating device 100B in FIG. 1B) is atomized so that aerosol is generated.

The second circuit 204 is used to obtain a value of a voltage applied to the load 132, a value relating to a resistance value of the load 132, a value of a voltage applied to the resistance 212, and so on. The case that the sensors 112B and 112D included in the second circuit 204 are voltage sensors, as shown in FIG. 2, will be considered as an example. When the switch Q2 is being in an ON state and the second circuit 204 is functioning, current flows through the switch Q2, the resistance 212, and the load 132. The value of the voltage applied to the load 132 and the value of the voltage applied to the resistance 212 are obtained by the sensors 112B and 112D, respectively. Further, it is possible to obtain the value of current flowing through the load 132 by using the value of the voltage applied to the resistance 212, that is obtained by the sensor 112D, and a known resistance value $R_{shunt}$ of the resistance 212. Since a total value of the resistance values of the resistance 212 and the load 132 can be obtained based on an output voltage $V_{out}$ of the conversion unit 208 and the above current value, a resistance value $R_{HTR}$ of the load 132 can be obtained by subtracting the known resistance value $R_{shunt}$ from the above total value. In the case that the load 132 has a positive or negative temperature-coefficient characteristic so that the resistance value changes according to temperature, it is possible to estimate temperature of the load 132 based on relationship between resistance values of the load 132 and temperature, that has been known in advance, and the resistance value $R_{HTR}$ of the load 132, that is obtained as explained above. It will be understood by a person skilled in the art that the resistance value and the temperature of the load 132 can be estimated by using the value of current flowing through the resistance 212. The values relating to the resistance value of the load 132 in this example may include a voltage value and a current value of the load 132 and so on. Tangible examples of the sensors 112B and 112D are not limited to voltage sensors, and they may include other elements such as current sensors (for example, Hall elements).

The sensor 112A detects an output voltage of the electric power source 110. The sensor 112C detects an output voltage of the conversion unit 208. Alternatively, the output voltage of the conversion unit 208 may be a predetermined target voltage. These voltages are those applied to the whole circuit.

The resistance value $R_{HTR}$ of the load 132 when the temperature of the load 132 is $T_{HTR}$ can be represented as follows:

$$R_{HTR}(T_{HTR})=(V_{HTR} \times R_{shunt})/(V_{Batt}-V_{HTR}) \quad (1)$$

In the above representation, $V_{Batt}$ is a voltage applied to the whole circuit. In the case that the conversion unit 208 is not used, $V_{Batt}$ is the output voltage of the electric power source 110. In the case that the conversion unit 208 is used, $V_{Batt}$ corresponds to an output voltage $V_{out}$ of the conversion unit 208 or a target voltage. $V_{HTR}$ is a voltage applied to the heater. Instead of $V_{HTR}$, the voltage applied to the shunt resistance 212 may be used.

In this regard, the circuit included in the aerosol generating device 100A may comprise, in place of one of or in addition to the above sensors, a temperature sensor which directly outputs a value corresponding to the temperature of the load 132.

2 Process for Determining Occurrence of Depletion or Shortage of Aerosol Source Regarding the process explained below, explanation thereof will be provided under the supposition that the control unit 106 executes all steps. However, it should be reminded that part of the steps may be executed by a different component in the aerosol generating device 100.

2-1 Outline of Process

Figure 3A:
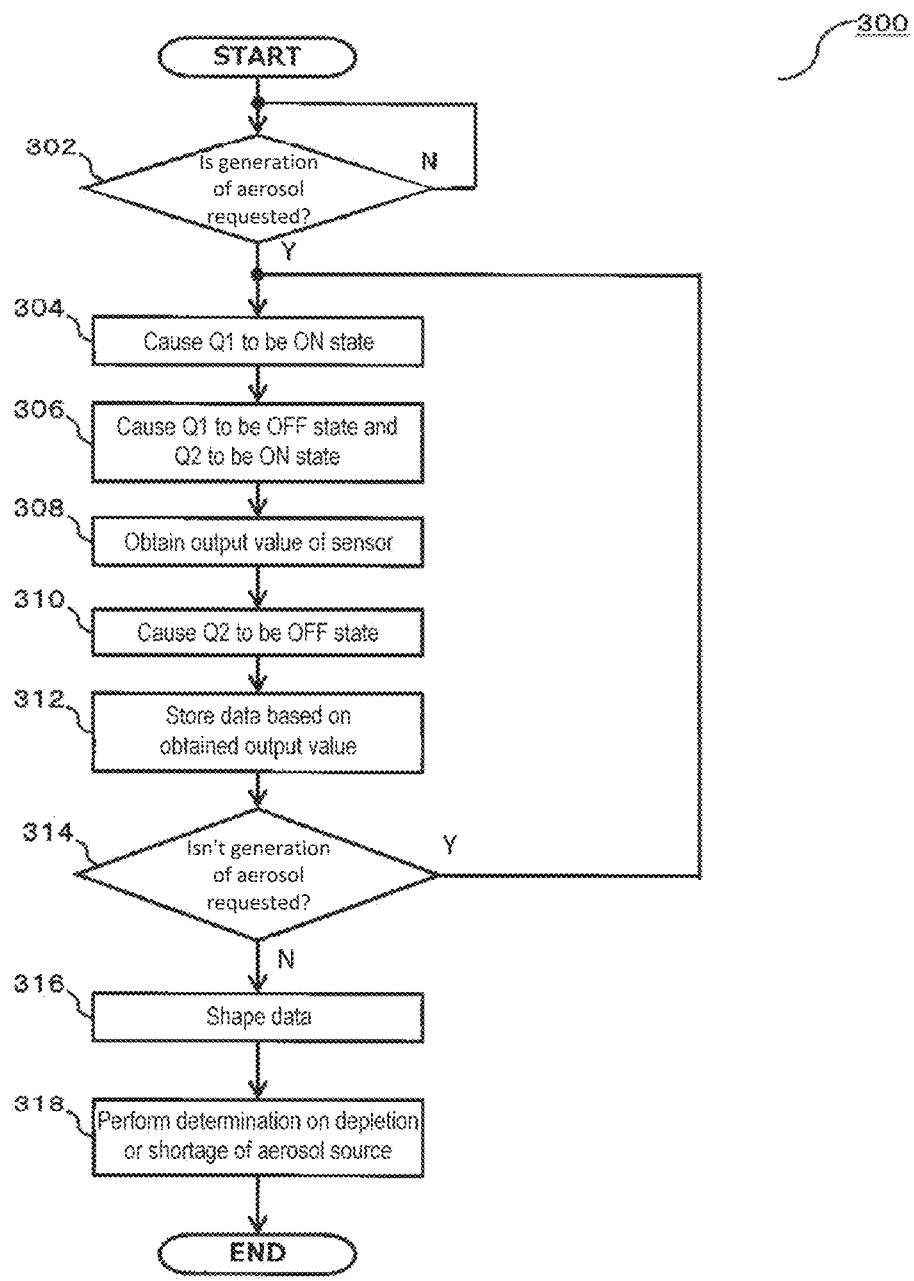
FIG. 3A is a flow chart of an example process for determining occurrence of depletion or shortage of an aerosol source according to an embodiment of the present disclosure.

FIG. 3A is a flow chart of an example process 300 for determining occurrence of depletion or shortage of an aerosol source according to an embodiment of the present disclosure.

It should be reminded that the phrase that the remaining quantity of the aerosol source is "depleted" means the state that the remaining quantity of the aerosol source is zero or almost zero.

Also, in the present disclosure, the phrase that the remaining quantity of the aerosol source is "short" means the state that the remaining quantity of the aerosol source is not sufficient, however, has not been depleted. Also, it may mean the state that the remaining quantity of the aerosol source is sufficient for instantaneous aerosol generation, although the remaining quantity of the aerosol source is insufficient for continuous aerosol generation.

When the aerosol source in the aerosol base material 116B or the holding unit 130 (hereinafter, they will be referred to as "the holding unit or the like") is in a saturation state, the temperature of the load 132 enters a steady state at a boiling point of the aerosol source or at temperature whereat generation of aerosol occurs as a result of vaporization of the aerosol source (hereinafter, they will be referred to as "the boiling point or the like"). In this regard, in the case that the remaining quantity of the aerosol source is equal to or more than a certain quantity although the aerosol source is not in the saturation state in the holding unit or the like, the temperature of the load 132 also enters a steady state at the boiling point or the like. In the present disclosure, the phrase that the remaining quantity of the aerosol source is "sufficient" in terms of the holding unit or the like means the state that the remaining quantity of the aerosol source in the holding unit or the like is equal to or more than the certain quantity, or the state that the remaining quantity of the aerosol source in the holding unit or the like is approximately the quantity that allows the temperature of the load 132 to enter a steady state at the boiling point or the like (the state includes a saturation state). It should be reminded that, in the latter case, it is not necessary to identify a tangible remaining quantity of the aerosol source in the holding unit or the like. Further, the boiling point of the aerosol source and the temperature whereat generation of aerosol occurs coincide with each other, if the aerosol source is a liquid comprised of a single composition. On the other hand, if the aerosol source is a liquid mixture, a theoretical boiling point of the liquid mixture obtained by using Raoult's law may be regarded as the temperature whereat generation of aerosol occurs, or the temperature whereat generation of aerosol occurs as a result of boiling of the aerosol source may be obtained by performing an experiment.

Further, in the case that the remaining quantity of the aerosol source in the storage unit 116A is less than the certain quantity, supply of the aerosol source from the storage unit 116A to the holding unit 130 is stopped, in principle (there may be a case that a very small quantity of the aerosol source is supplied, or a case that a small quantity of the aerosol source is supplied as a result that the aerosol generating device 100 is tilted, shook, or the like). In the present disclosure, the phrase that the remaining quantity of the aerosol source is "sufficient" in terms of the storage unit 116A means the state that the remaining quantity of the aerosol source in the storage unit 116A is equal to or more than the certain quantity, or the state that the remaining quantity is approximately the quantity that allows the aerosol source in the holding unit 130 to enter a saturation state, or allows supply of the aerosol source to increase the remaining quantity of the aerosol source therein to a quantity equal to or greater than the certain quantity. It should be reminded that, in the latter case, it is not necessary to identify a tangible remaining quantity of the aerosol source in the storage unit 116A, since it is possible to estimate the state that the remaining quantity or aerosol source in the storage unit 116A is sufficient, by detecting the state that the temperature of the load 132 has been entered a steady state at the boiling point or the like.

302 denotes a step of determining whether a request for generation of aerosol has been made. For example, when the control unit 106 has detected a start of inhalation of a user based on information obtained from a pressure sensor, a flow rate sensor, or the like, it is possible to determine that a request for generation of aerosol has been made. More specifically, for example, the control unit 106 can determine that a start of inhalation by a user is detected, when an output value of the pressure sensor, i.e., the pressure, is below a predetermined threshold value. Further, for example, the control unit 106 can determine that a start of inhalation by a user is detected, when an output value of the flow rate sensor, i.e., the flow quantity or the flow speed, exceeds a predetermined threshold value. In the above determination method, a flow rate sensor is especially preferable, since aerosol generation suitable to user's feeling can be performed. Alternatively, the control unit 106 can determine that a start of inhalation by a user is detected, when output values of these sensors start to change continuously. Alternatively, the control unit 106 can determine that a start of inhalation by a user is detected, based on a state that a button for starting generation of aerosol has been pushed, or the like. Alternatively, the control unit 106 can determine that a start of inhalation by a user is detected, based on both the information obtained from the pressure sensor or the flow rate sensor and the action to push the button.

If it is determined that a request for generation of aerosol has been made, the process proceeds to step 304, and, if not, the process returns to step 302.

304 denotes a step of causing the switch Q1 to be an ON state. By performing this step, current flows to the load 132 through the switch Q1, and the load 132 is heated as a result.

306 denotes a step of causing the switch Q1 to be an OFF state, and causing the switch Q2 to be an ON state. By performing this step, current flows to the shunt resistance 212 and the load 132 through the switch Q2.

308 denotes a step of obtaining an output value of a sensor. The sensor can be any sensor which can output a value relating to the temperature of the load 132, and may comprise one of or both the sensor 112B and 112D, for example.

310 denotes a step of causing the switch Q2 to be an OFF state.

312 denotes a step of storing data based on the output value obtained in step 308.

The "data based on the output value obtained in step 308" may be the output value itself obtained in step 308, or a value derived from the output value obtained in step 308. For example, in the case that the output value is a voltage value obtained from the voltage sensor 112D, the "value derived from the output value" may be the resistance value of the load 132 derived from the voltage value. For example, in the case that the output value is a voltage value obtained from the voltage sensor 112D, the "value derived from the output value" may be an average of plural voltage values obtained from the voltage sensor 112D or a value derived from the average.

In step 312, it is necessary to store the data in the form that can show the order that pieces of the data are stored. Preferably, each piece of data can be stored in association with the time when an output value, that is the basis of the piece of data, is obtained. The time may be a relative time, for example, a relative time that uses, as the reference time, the time when it is determined in step 302 that a request for generation of aerosol has been made. In this regard, it should be reminded that, even if pieces of data are stored merely in a manner that the order that the pieces of data are stored can be seen, relative time relating to each piece of data can be estimated later, if the time required for executing a loop that starts from step 304 and returns to step 304 via step 314, that will be explained later, has been known. The time may be an absolute time that is a current time, instead of a relative time explained above.

314 denotes a step of determining whether a request for generation of aerosol has not been made. For example, when the control unit 106 has detected an end of inhalation of a user based on information obtained from a pressure sensor, a flow rate sensor, or the like, it is possible to determine that a request for generation of aerosol has not been made. In this regard, for example, the control unit 106 can determine that an end of inhalation by a user is detected, in other words, a request for generation of aerosol has not been made, when an output value of the pressure sensor, i.e., the pressure, exceeds a predetermined threshold value. Further, for example, the control unit 106 can determine that an end of inhalation by a user is detected, in other words, a request for generation of aerosol has not been made, when an output value of the flow rate sensor, i.e., the flow quantity or the flow speed, is below a predetermined threshold value that may be 0. In this regard, the threshold value may be greater than the threshold value in step 302, or equal to the above threshold value, or smaller than the above threshold value. Alternatively, the control unit 106 can determine that an end of inhalation by a user is detected, in other words, a request for generation of aerosol has not been made, based on a state that a button for starting generation of aerosol has been released, or the like. Alternatively, the control unit 106 can determine that an end of inhalation by a user is detected, in other words, a request for generation of aerosol has not been made, when a predetermined condition such as a condition that a predetermined period of time has elapsed since a button for starting generation of aerosol is pushed, or the like is satisfied.

If it is determined that a request for generation of aerosol has not been made, the process proceeds to step 316, and, if not, the process returns to step 304.

316 denotes a step of shaping data stored in step 312, for example, excluding a predetermined part of the data or the like. In this regard, the "predetermined part of the data" may be parts corresponding to a heating period and a cooling period relating to the load 132, for example. That is, according to step 316, shaped data, from which parts corresponding to the heating period and the cooling period have been excluded, can be used in step 318 that will be explained later.

In the following description, temperature change in the load 132 will be explained with reference to FIG. 4A.

Figure 4A:
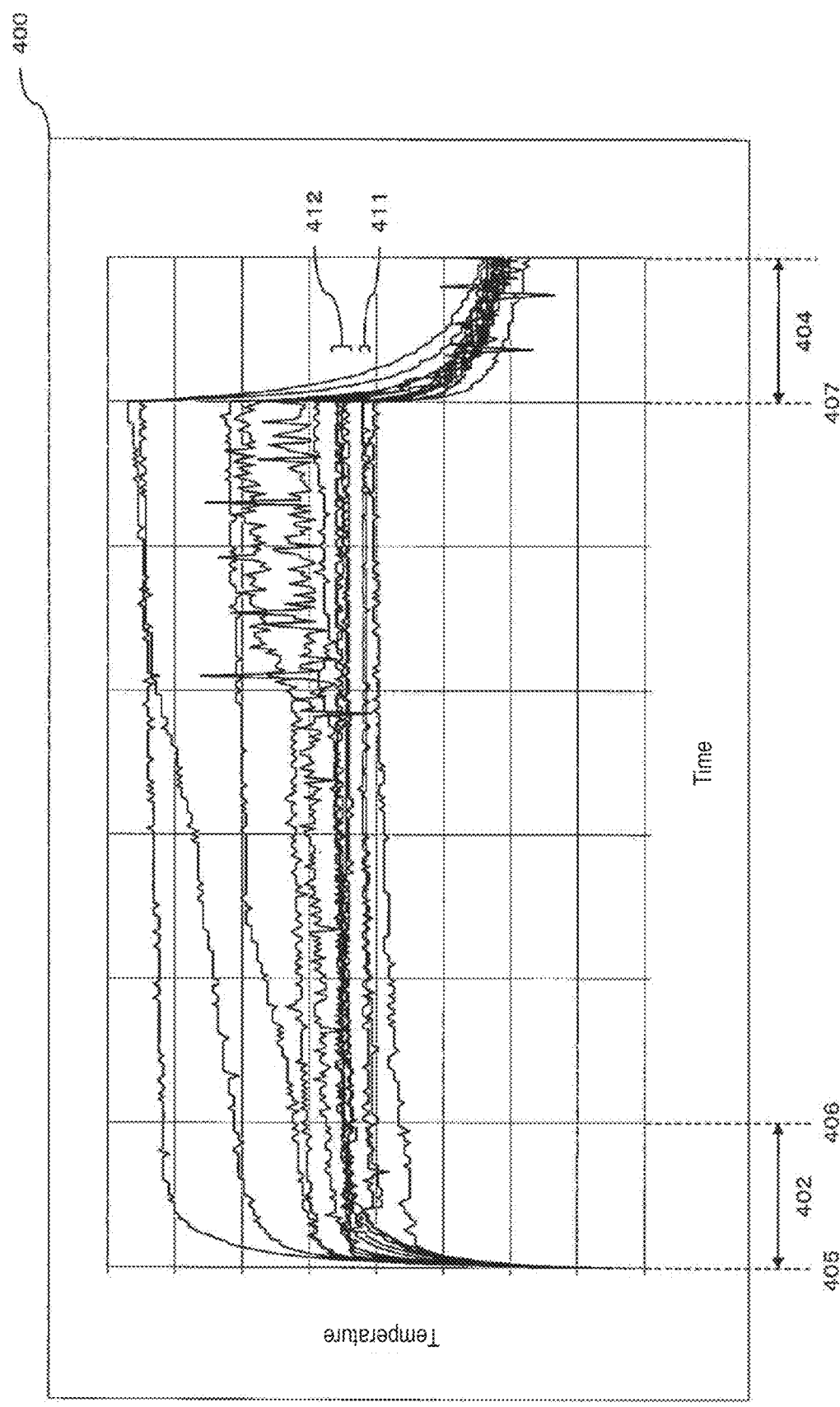
FIG. 4A is a graph in which temperature of a load in each electric power supplying cycle is plotted.

FIG. 4A is a graph 400 in which temperature of the load 132 versus time in each electric power supplying cycle is plotted. In the following description, temporal change in temperature that is represented by plotting the temperature to correspond to respective points in time is referred to as a temperature profile. The horizontal axis of the graph 400 represents relative time that is defined by using, as a reference, the time when it is determined in step 302 that a request for generation of aerosol has been made, and the vertical axis represents temperature of the load 132. In this regard, time 407 corresponds to the time when it is determined in step 314 that a request for generation of aerosol has not been made. Each temperature profile corresponds to each electric power supplying cycle.

A single electric power supplying cycle is a period that includes at least a period that starts when continuous or intermittent substantial supply of electric power to the load 132 is started in response to an event that a request for generation of aerosol is made, and ends when the making of the request for generation of aerosol is discontinued, or substantial supply of electric power to the load 132 is ended in response to discontinuation of the making of the request for generation of aerosol.

Thus, a single electric power supplying cycle may be a period from the time when it is determined in step 302 that a request for generation of aerosol has been made to the time when it is determined in step 314 that a request for generation of aerosol has not been made. In the following description, it is supposed that a single electric power supplying cycle starts from the time 405 that is the time when it is determined in step 302 that a request for generation of aerosol has been made; however, the configuration is not limited to that explained above. For example, a single electric power supplying cycle may start from a time before the time when it is determined in step 302 that a request for generation of aerosol has been made.

Further, strictly speaking, the time when it is determined in step 302 that a request for generation of aerosol has been made and the time when substantial supply of electric power to the load 132 is started are different from each other. A single electric power supplying cycle may start when substantial supply of electric power to the load 132 is started after a request for generation of aerosol is made in step 302, for example, when or before supply of electric power, electric energy of electric energy, supply of current, or application of a voltage greater than a predetermined threshold value (that includes 0) to the load 132 is actually performed.

Alternatively, a single electric power supplying cycle may be a period from the time when it is determined in step 302 that a request for generation of aerosol has been made to the time when it is determined in next step 302 that a request for generation of aerosol has been made.

It should be reminded that the lengths of respective electric power supplying cycles may be different from each other, or the same with each other. Since a single electric power supplying cycle may occur as a result of a single inhalation action (a puff) of a user using the aerosol generating device 100, it is referred to as a single puff.

402 denotes an example heating period. The heating period is a period from a time when rising of the temperature of the load 132 starts to a time when temperature change becomes stable or the temperature of the load 132 reaches a predetermined temperature. Whether the temperature of the load 132 has become stable may be determined based on a time differential value of the temperature of the load 132, a difference between the last temperature and the present temperature, or the like. In the graph 400, it is supposed that the heating period is a period from the time 405, that is the time when it is determined in step 302 that a request for generation of aerosol has been made, to the time 406 that has been set in such a manner that the period has a sufficient margin.

The heating period may be that obtained manually by making and using a graph such as the graph 400 in advance. In the above case, it should be reminded that the lengths of the heating periods in respective electric power supplying cycles become the same. Alternatively, the heating period may be a period that is determined by determining, by the control unit 106 by using an arbitrary method, the time when rising of the temperature of the load 132 starts and the time when temperature change becomes stable. For example, the control unit 106 may determines, as the former time, the time when it is determined in step 302 that a request for generation of aerosol has been made, and determines, as the latter time, the time when the temperature rising rate (temperature rise per unit time) of the load 132 becomes a value equal to or lower than a predetermined threshold value, or when each of a predetermined number of them in succession becomes a value equal to or lower than a predetermined threshold value. Alternatively, it may be possible to determine, as the latter time, the time when a difference between the last-obtained temperature of the load 132 and the most-recently-obtained temperature of the load 132 becomes a value equal to or lower than a predetermined threshold value. Alternatively, it may be possible to determine, as the latter time, the time when a standard deviation or variance of plural values of the temperature of the load 132 obtained in a most recent period becomes a value equal to or lower than a predetermined threshold value. It should be reminded that, in the above cases, the lengths of the heating periods in respective electric power supplying cycles may change according to various conditions such as individual differences between the cartridges 104A and the aerosol generating articles 104B, ambient temperature, and so on.

404 denotes part of example cooling period. The cooling period is a period from a time when decreasing of the temperature of the load 132 starts to a time when temperature change becomes stable or the temperature reaches a predetermined temperature. Alternatively, the cooling period may be ended when a next electric power supplying cycle of a next heating period starts. In the graph 400, it is supposed that the cooling period starts from the time 407 that is the time when it is determined in step 314 that a request for generation of aerosol has not been made.

The cooling period may be that obtained manually by making and using a graph such as the graph 400 in advance. In the above case, it should be reminded that the lengths of the cooling periods in respective electric power supplying cycles become the same. Alternatively, the cooling period may be a period that is determined by determining, by the control unit 106 by using an arbitrary method, the time when decreasing of the temperature of the load 132 has started and the time when the temperature has reached a predetermined temperature. For example, the control unit 106 may determines, as the former time, the time when it is determined in step 314 that a request for generation of aerosol has not been made, and determines, as the latter time, the time when the temperature of the load 132 has become a value equal to or lower than a predetermined threshold value, or when each of a predetermined number of temperature values in succession becomes a value equal to or lower than a predetermined threshold value. Alternatively, it may be possible to determine, as the latter time, the time when a difference between the last-obtained temperature of the load 132 and the most-recently-obtained temperature of the load 132 becomes a value equal to or lower than a predetermined threshold value. Alternatively, it may be possible to determine, as the latter time, the time when a standard deviation or variance of plural values of the temperature of the load 132 obtained in a most recent period becomes a value equal to or lower than a predetermined threshold value. It should be reminded that, in the above cases, the lengths of the cooling periods in respective electric power supplying cycles may change according to various conditions such as individual differences between the cartridges 104A and the aerosol generating articles 104B, ambient temperature, and so on.

In the example process 300, data is not stored after the time when it is determined in step 314 that a request for generation of aerosol has not been made; however, the process of the present disclosure for determining depletion or shortage of the aerosol source may not exclude a different process for obtaining an output value from a sensor and storing data, that is to be executed after the time when it is determined in a step corresponding to step 314 that a request for generation of aerosol has not been made. Thus, in such a different example, a "predetermined part" in the step corresponding to step 316 may include a cooling period.

Further, the "predetermined part" in step 316 may be part corresponding to one or more of the time of a start of an electric power supplying cycle, the time of an end of an electric power supplying cycle, one or more arbitrary points in time in an electric power supplying cycle, and arbitrary part of, i.e., an arbitrary period of time in the duration of, an electric power supplying cycle. Thus, according to step 316, data, which includes data corresponding to that at the time of a start of the electric power supplying cycle and does not include data right after the above data, for example, can be used in step 318 that will be explained later. Further, parts corresponding to one or more parts in the above-explained arbitrary period of time in an electric power supplying cycle may include the time when an electric power supplying cycle starts and the time when an electric power supplying cycle ends. In the above case, a predetermined period starting from the time of a start of an electric power supplying cycle or a predetermined period going back from the time of an end of an electric power supplying cycle corresponds to the "predetermined part."

318 denotes a step of perform, based on data which does not include data excluded in step 316, determination on depletion or shortage of the aerosol source. It should be reminded that the phrase "based on data" includes the meaning "based on at least part of data."

Figure 3B:
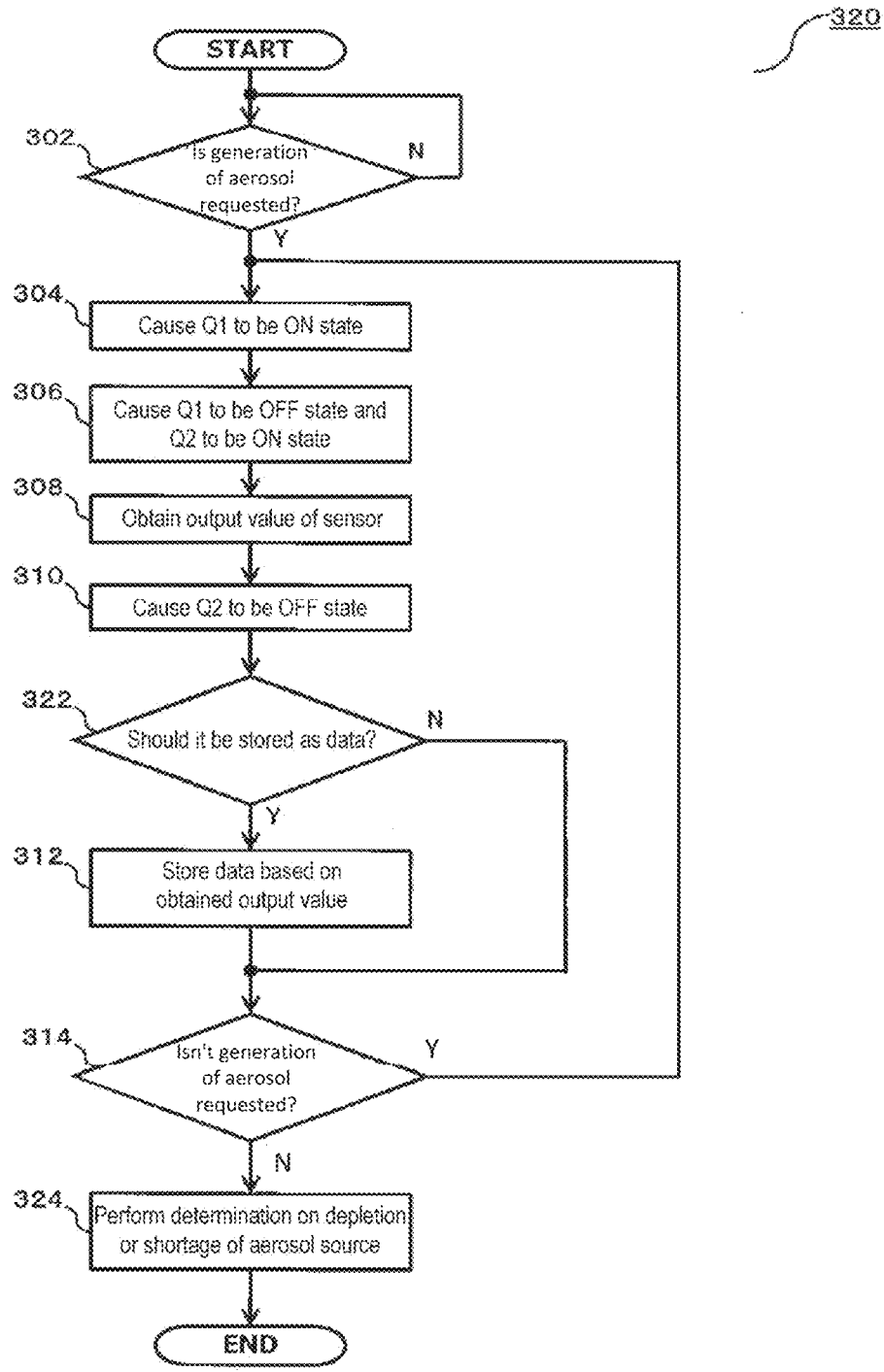
FIG. 3B is a flow chart of a different example process for determining occurrence of depletion or shortage of an aerosol source according to an embodiment of the present disclosure.

FIG. 3B is a flow chart of a different example process 320 for determining occurrence of depletion or shortage of an aerosol source according to an embodiment of the present disclosure. Since some steps included in the example process 320 are the same as those included in the example process 300, steps that are not included in the example process 300 will be explained in the following description.

322 denotes a step of determining whether data, that is based on the output value of the sensor obtained in step 308, should be stored. If it is determined that the above data is data that should be stored, the process proceeds to step 312, and, if not, the process proceeds to step 314.

In step 322, it is possible to determine that the above data should not be stored as data, if the output value of the sensor obtained in step 308 corresponds to the predetermined part that has been explained above in relation to step 316. That is, according to step 322, it becomes possible to prevent, in advance, storing of data corresponding to a heating period, a cooling period, or the like in step 312. As a result, the cost, weight, and size of the aerosol generating device 1000 can be reduced, since the required storage capacity of the memory 114 can be reduced. Further, since step 316 is not necessary in the example process, determination on depletion or shortage of the aerosol source in step 314 can be performed faster.

324 denotes a step of performing, based on data stored in step 312, determination on depletion or shortage of the aerosol source.

Figure 5:
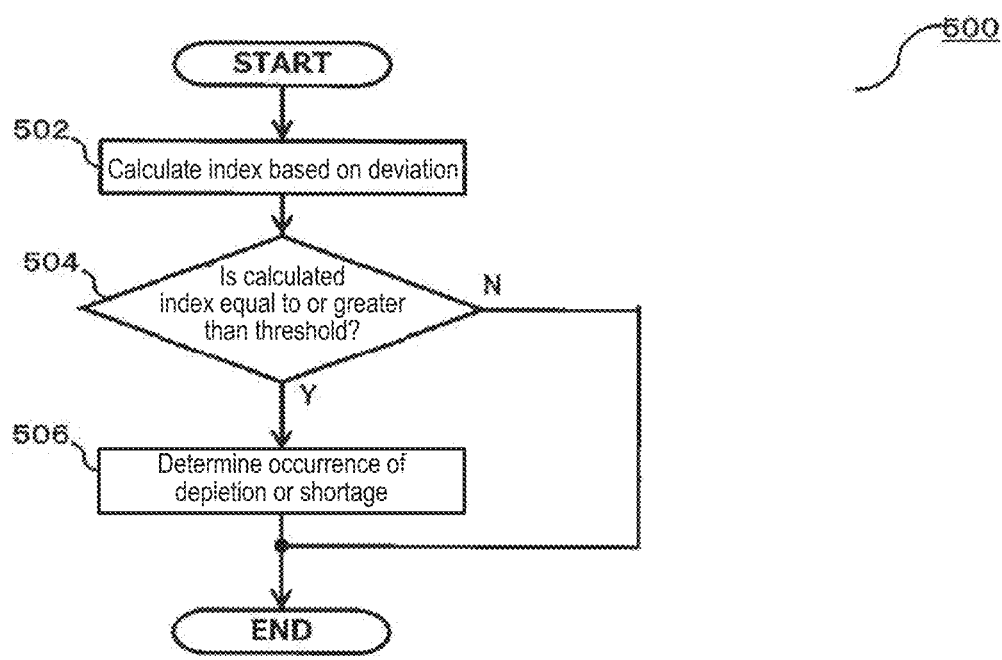
FIG. 5 is a flow chart of a first example process for performing determination on depletion or shortage of an aerosol source according to an embodiment of the present disclosure.

2-2 First Example Process for Determining Occurrence of Depletion or Shortage of Aerosol Source FIG. 5 is a flow chart of a first example process 500 executed in step 318 or 324.

502 denotes a step of calculating an index based on a deviation of the output value of the sensor obtained in step 308. The "index based on a deviation" may be a standard deviation or variance, for example.

Step 502 is a step of calculating the above index based on data (hereinafter, this will be referred to as "calculation data") that is based on the output value of the sensor and does not include some parts of original data excluded in step 316 or step 322. In this regard, the above index may be calculated from the calculation data itself, or calculated form a value derived from the calculation data.

Thus, for example, if the data stored in step 308 is the output value of the sensor itself, the calculation data, i.e., the standard deviation of the output values, is obviously "the index based on the deviation of the output values of the sensor."

Further, for example, in the case that the sensor outputs a voltage value and the resistance value of the load 132 derived from the voltage value is stored as data in step 308, a statistical characteristic of the calculation data, i.e., the value of the temperature of the load 132 derived from the resistance value, is the same as the voltage value outputted form the sensor, so that the standard deviation of such temperature values of the load 132 is "the index based on the deviation of the output values of the sensor," finally.

Thus, the indexes based on output values of the sensor may be indexes based on deviations of various types of physical quantities, that are derived only from output values of the sensor in each electric power supplying cycle, in other words, the index may be an index based on a deviation that can be generated from a single electric power supplying cycle.

504 denotes a step of determining whether the index calculated in step 502 is equal to or greater than a predetermined threshold. If the index calculated in step 502 is equal to or greater than the predetermined threshold, the process proceeds to step 506, and, if not, the process is terminated. In this regard, if the index calculated in step 502 represents a value that becomes larger as the dispersion of calculation data becomes larger, like a standard deviation, the process in step 504 may be that for determining whether the index is equal to or greater than a threshold value. On the other hand, it should be reminded that, if the index calculated in step 502 represents a value that becomes smaller as the dispersion of calculation data becomes larger, the process in step 504 may be that for determining whether the index is equal to or smaller than a threshold value.

506 denotes a step of determining that depletion or shortage of the aerosol source in the storage unit 116A or the aerosol base material 116B (hereinafter, they will be referred to as "the storage unit or the like") has occurred.

In the following description, judgment of depletion or shortage of the aerosol source in an example process 500 will be explained with reference to FIG. 4B and FIG. 6.

Figure 4B:
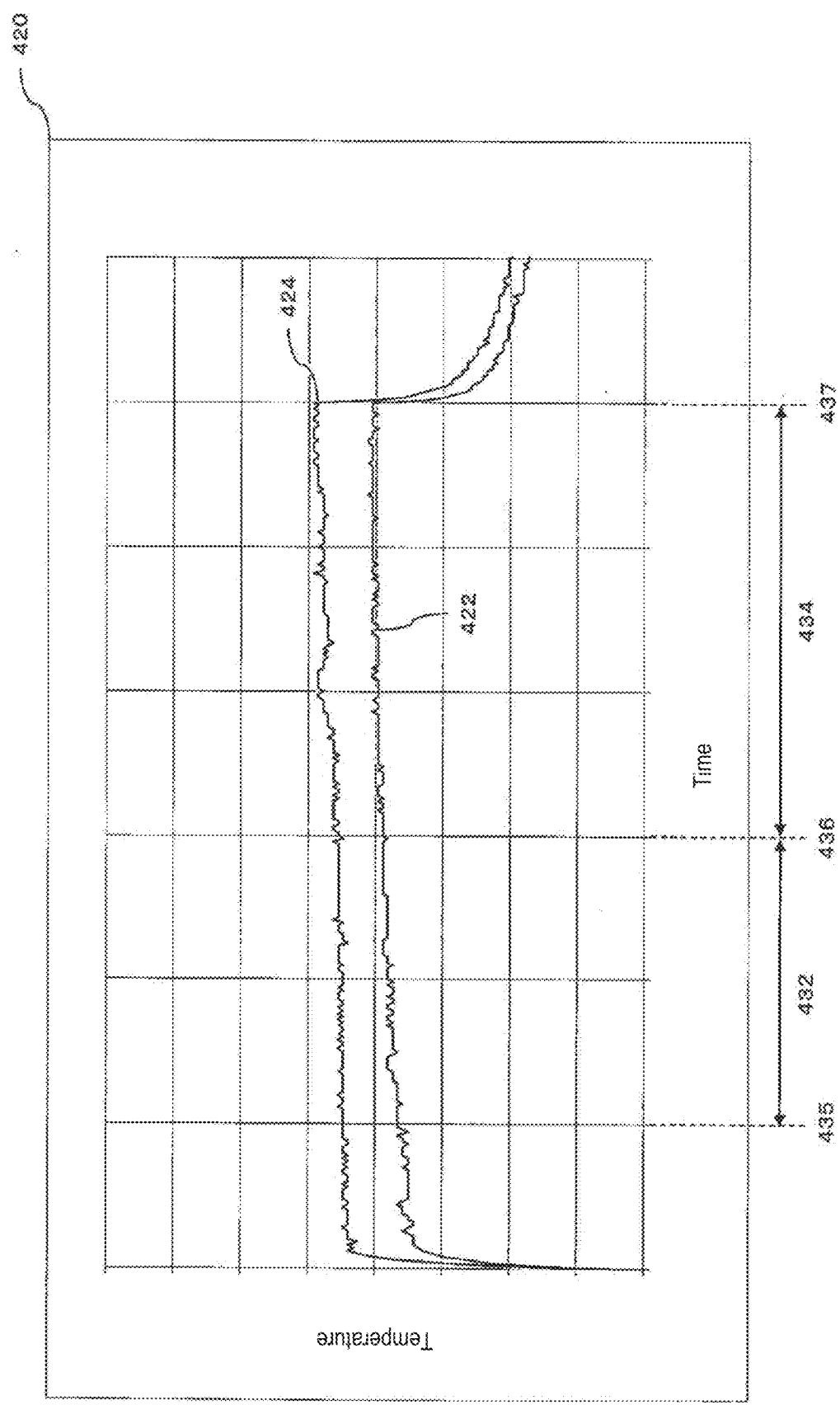
FIG. 4B is a graph in which temperature of a load in two electric power supplying cycles is plotted.

FIG. 4B represents a graph 420 in which a temperature profile 422 in an electric power supplying cycle when the remaining quantity of the aerosol source in the holding unit or the like is sufficient and a temperature profile 424 when the remaining quantity is insufficient, in the temperature profiles included in the graph 400, are plotted. Especially, the electric power supplying cycle corresponding to the temperature profile 424 is an electric power supplying cycle during which first occurrence of a change of color in the load 132 due to a burnt deposit or oxidation has been visually confirmed; and, the above means that the remaining quantity of the aerosol source in the holding unit or the like has been depleted in the middle of this electric power supplying cycle.

Regarding the above matter, the case of the configuration shown in FIG. 1A will be studied; and, in such a case, if the remaining quantity of the aerosol source in the storage unit 116A is sufficient, the remaining quantity of the aerosol source in the holding unit 130 will be sufficient. However, if the remaining quantity of the aerosol source in the storage unit 116A is in short supply, supply thereof will be stagnated, and depletion or shortage of the remaining quantity of the aerosol source in the holding unit 130 will occur. Especially, supply will be completely stopped if depletion of the remaining quantity of the aerosol source in the storage unit 116A has occurred, and, as a result, the aerosol source in the holding unit 130 will be depleted. Put another way, when the remaining quantity of the aerosol source in the holding unit 130 has been depleted, the remaining quantity of the aerosol source in the storage unit 116A has been depleted or in short supply.

Further, the case of the configuration shown in FIG. 1B will be studied; and, in such a case, as explained above, the remaining quantity of the aerosol source in the aerosol base material 116B is depleted in the electric power supplying cycle corresponding to the temperature profile 424.

Thus, in the electric power supplying cycle corresponding to the temperature profile 424, the remaining quantity of the aerosol source in the storage unit or the like is depleted or in short supply.

When the temperature profile 422 is compared with the temperature profile 424, it can be understood that fluctuation of the temperature of the load 132 in the temperature profile 424, that corresponds to the electric power supplying cycle during which the remaining quantity of the aerosol source in the holding unit or the like is depleted, is larger than the other. In the example process 500 that will be explained later, fluctuation of the temperature of the load 132 is evaluated by using a standard deviation or the like. By the way, if extremely low temperature of the load 132 in the heating period and/or a cooling period is included in samples used for deriving a standard deviation, the value of the standard deviation will be changed greatly. Thus, it will be understood that the above-explained process in step 316 or step 322 is important for evaluating fluctuation of the temperature of the load 132 by using a standard deviation.

An electric power supplying cycle may comprise plural phases. In this regard, the lengths of respective phases may be the same with each other or different from each other. Further, at least parts of phases may overlap with each other. In this regard, it is possible to consider that part of the plural phases corresponds to one of or both the heating period and the cooling period that are explained above. 432 denotes an example of a first phase that is a phase in the plural phases. 434 denotes an example of a second phase that is a phase in the plural phases and appears after the first phase in a time series. It should be reminded that, although the first phase 432 and the second phase 434 are adjacent to each other in the graph 420, there may be one or more phases between the first phase 432 and the second phase 434. Further, the first phase 432 and the second phase 434 may partially overlap with each other. It is supposed in FIG. 4B that the first phase 432 and the second phase 434 are a period from the time 435 (this time is the same as the time 406 in FIG. 4A in this example) to the time 436 and a period from the time 436 to the time 437 (this time is the same as the time 407 in FIG. 4A in this example), respectively.

Figure 6:
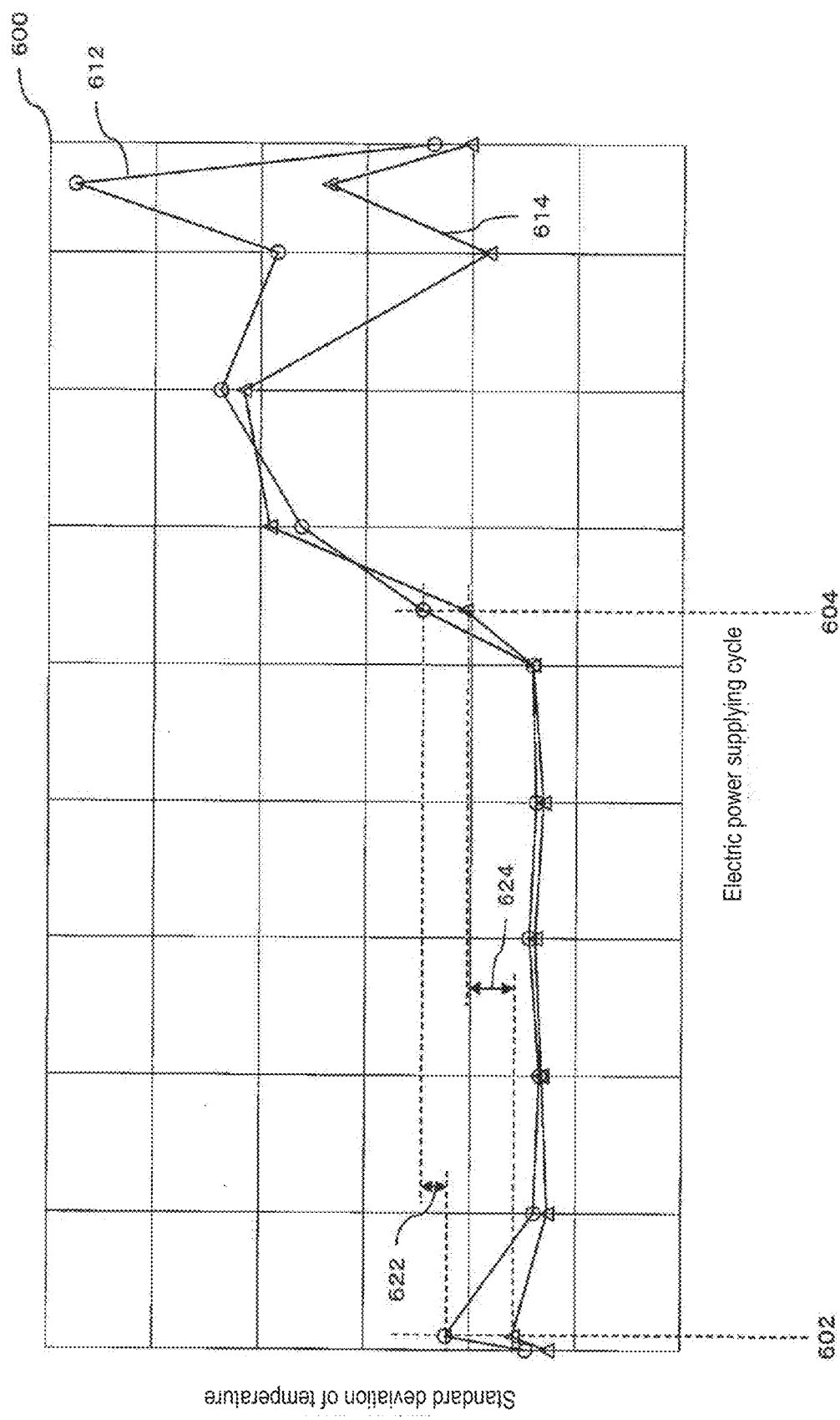
FIG. 6 is a graph in which standard deviations of temperature of a load relating to respective electric power supplying cycles are plotted.
Figure 7:
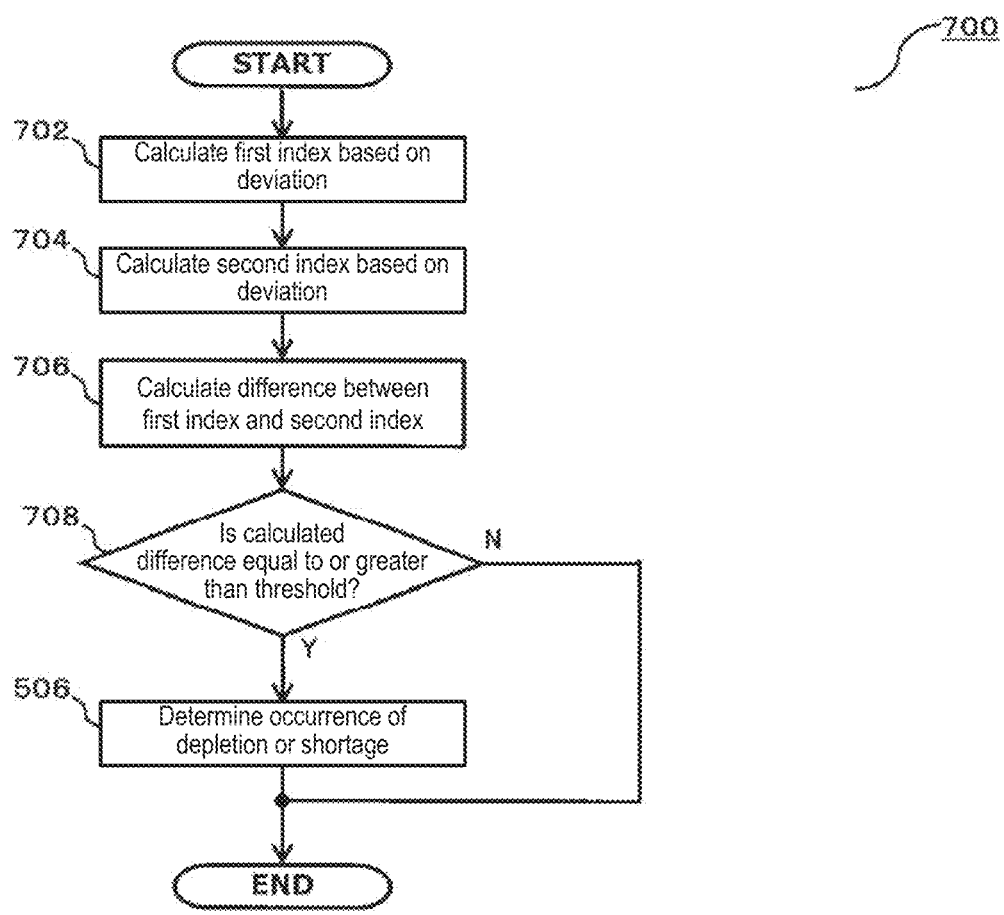
FIG. 7 is a flow chart of a second example process for performing determination on depletion or shortage of an aerosol source according to an embodiment of the present disclosure.
Figure 8:
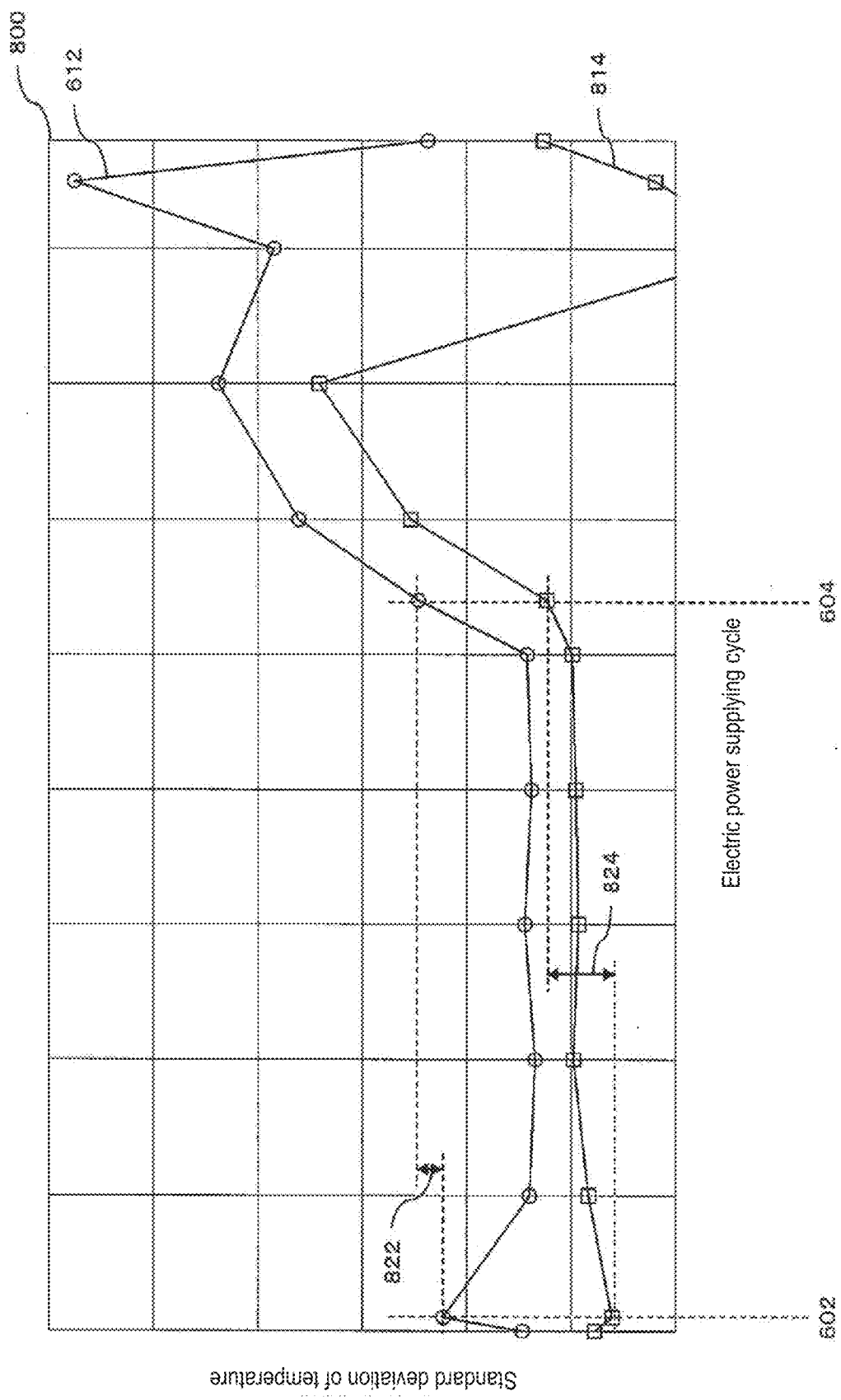
FIG. 8 is a graph in which standard deviations of temperature of a load relating to respective electric power supplying cycles are plotted.

FIG. 6 is a graph 600 relating to respective electric power supplying cycles, in which standard deviations of the temperature of the load 132 based on the calculation data versus respective electric power supplying cycles are plotted. Hereinafter, the plot of standard deviations plotted in relation to respective electric power supplying cycles is referred to as a standard deviation profile. The horizontal axis of the graph 600 represents the numbers of times of electric power supplying cycles, the vertical axis of the graph 600 represents standard deviations of the temperature of the load 132. 602 and 604 denote an electric power supplying cycle corresponding to the temperature profiles 422 and 424 in FIG. 4B, respectively. 612 denotes a standard deviation profile derived from calculation data corresponding to both the first phase 432 and the second phase 434. 614 denotes a standard deviation profile derived from calculation data corresponding to the second phase 434 only, in the first phase 432 and the second phase 434.

It is understood as a result of study with respect to respective standard deviation profiles that the standard deviation of the temperature in the electric power supplying cycle 604 is larger than the standard deviation in the electric power supplying cycle 602 that is the largest standard deviation of the temperature in electric power supplying cycles before the above electric power supplying cycle. As explained above, the electric power supplying cycle 604 is an electric power supplying cycle during which the remaining quantity of the aerosol source in the holding unit or the like is depleted, and corresponding to the temperature profile 424. Further, an electric power supplying cycle before the electric power supplying cycle 604 corresponds to a temperature profile corresponding to a state that the remaining quantity of the aerosol source in the holding unit or the like is sufficient, or a state that the remaining quantity is not sufficient but has not been depleted. As explained above, in a state that the remaining quantity of the aerosol source in the holding unit or the like is sufficient, the state of the temperature of the load 132 becomes a steady state at the boiling point or the like. Similarly, even in a state that the remaining quantity of the aerosol source in the holding unit or the like is not sufficient but has not been depleted, the state of the temperature of the load 132 becomes a steady state at the boiling point or the like (this will be explained in section 3-2). Thus, in an electric power supplying cycle before the electric power supplying cycle 604, there is tendency that the standard deviation of the temperature shows a small value. On the other hand, in an electric power supplying cycle, such as the electric power supplying cycle 604, during which the remaining quantity of the aerosol source in the holding unit or the like is depleted, the quantity of aerosol source in the whole part or a local part of the holding unit or the like becomes extremely small. That is, unevenness in temperature occurs in the load 132, according to distribution of the aerosol source in the holding unit or the like. It is considered that, due to fluctuation of the temperature of the load 132 due to the above temperature unevenness, the standard deviation of the temperature in the electric power supplying cycle 604 shows a large value. In addition, it is considered that, since the aerosol source does not function as a refrigerant for the load 132, color change of the load 132 progresses further or the like in an electric power supplying cycle after the electric power supplying cycle 604, the standard deviation of the temperature in the electric power supplying cycle 604 shows a larger value.

The above matter means that occurrence of depletion or shortage of the aerosol source in the storage unit or the like can be determined in step 506, by setting the predetermined threshold value in step 504 to a value that is equal to or lower than a standard deviation of temperature in an electric power supplying cycle (for example, the standard deviation of the temperature in the electric power supplying cycle 604) at the time when the aerosol source in the storage unit or the like is depleted or in short supply (an electric power supplying cycle during which the aerosol source in the holding unit or the like is depleted), and also larger than the maximum standard deviation of temperature in an electric power supplying cycle (for example, the standard deviation of the temperature in the electric power supplying cycle 602) at the time different from the above time.

Further, it is understood, when the standard deviation profiles 612 and 614 are compared with each other, that the difference 624 between the standard deviation in the electric power supplying cycle 602 and the standard deviation in the electric power supplying cycle 604 with respect to the latter is larger than the difference 622 between the standard deviation in the electric power supplying cycle 602 and the standard deviation in the electric power supplying cycle 604 with respect to the former. The above matter means that, regarding the difference between a state when the remaining quantity of the aerosol source in the storage unit or the like has been depleted or in short supply and a state when the remaining quantity has not been depleted or in short supply, the difference in the standard deviation profile 614, that is derived from the calculation data corresponding to the second phase 432 only, in the first phase 432 and the second phase 434, is larger. Thus, by appropriately setting part of calculation data used for deriving a standard deviation, it becomes possible to set, in step 504, a more preferable threshold value that is less susceptible to noise and so on.

In addition, regarding an event that a standard deviation of temperature in the electric power supplying cycle 602 shows a relatively large value, explanation of the reason thereof may be that the quantity of the aerosol source in the holding unit or the like has been increased excessively since the aerosol generating device 100 has been left for a long time and the temperature increase in the load 132 is disturbed accordingly in an early stage of the temperature profile, or the like.

2-3 Second Example Process for Determining Occurrence of Depletion or Shortage of Aerosol Source FIG. 7 is a flow chart of a second example process 700 executed in step 318 or 324. Since some steps included in the example process 700 are the same as those included in the example process 500, steps that are not included in the example process 500 will be explained in the following description.

702 and 704 denote steps for calculating a first index and a second index, that are based on deviations derived from output values obtained in step 308, respectively. Step 702 and 704 are similar to step 502, except for the calculation data used for deriving an index based on a deviation. Here, FIG. 4B is referred to again; and the calculation data used for deriving the first index in step 702 may be the calculation data corresponding to the first phase 432, and the calculation data used for deriving the second index in step 704 may be the calculation data corresponding to the second phase 434.

706 and 708 denote a step of calculating a difference between the first index and the second index and a step of determining whether the calculated difference is equal to or greater than a threshold value, respectively. It should be reminded that it is supposed in this example that each of the first index and the second index shows a value that becomes larger as the dispersion of the calculation data becomes larger, and the difference between the first index and the second index is calculated by subtracting the first index from the second index. It should be reminded that, in the case that a first index and a second index, each showing a value that becomes smaller as the dispersion of the calculation data becomes larger, is used, or in the case that the difference between the first index and the second index is calculated by subtracting the second index from the first index, step 708 may be configured to determine whether the calculated value is less than the threshold value.

In the following description, judgment of depletion or shortage of the aerosol source in the example process 700 will be explained with reference to FIG. 8.

FIG. 8 is a graph 800 in which standard deviations of the temperature of the load 132 derived from calculation data, that relate to respective electric power supplying cycles, are plotted, and the graph is similar to the graph 600. However, 814 denotes a standard deviation profile obtained by subtracting the first index from the second index.

It is understood, when the standard deviation profiles 612 and 814 are compared with each other, that the difference 824 between the standard deviation in the electric power supplying cycle 602 and the standard deviation in the electric power supplying cycle 604 with respect to the latter is larger than the difference 822 between the standard deviation in the electric power supplying cycle 602 and the standard deviation in the electric power supplying cycle 604 with respect to the former. That is, it becomes possible to set, in step 708, a more preferable threshold value that is less susceptible to noise and so on, by deriving the first index and the second index in such a manner that a difference between the standard deviation of temperature in an electric power supplying cycle at the time when the aerosol source in the storage unit or the like is depleted or in short supply (an electric power supplying cycle during which the aerosol source in the holding unit or the like is depleted) and the maximum standard deviation of temperature in an electric power supplying cycle at the time different from the above time becomes larger.

The event that the difference between the standard deviation in the electric power supplying cycle 602 and the standard deviation in the electric power supplying cycle 604 relating to the standard deviation profile 814 is larger than that relating to the standard deviation profile 612 can be explained as follows: It is considered that, in the electric power supplying cycle 602, although the temperature increase in the load 132 is disturbed in an early stage of the temperature profile as a result that the aerosol generating device 100 has been left for a long time, the temperature of the load 132 enters a steady state at the boiling point or the like stays therein in or after a middle stage of the temperature profile. That is, in the electric power supplying cycle 602, since the standard deviations in or after the middle stage in the heating profile are small, a value obtained by subtracting the first index, that corresponds to the former, from the second index, that corresponds to the latter, tends to show a small value. On the other hand, in the electric power supplying cycle 604, since the remaining quantity of the aerosol source in the holing unit or the like will be depleted in the middle of the cycle, the temperature of the load 132 tends to fluctuate. That is, in the electric power supplying cycle 604, the standard deviations in or after a middle stage in the heating profile are large. Thus, a value obtained by subtracting the first index, that corresponds to the former, from the second index, that corresponds to the latter, tends to show a large value.

Figure 9:
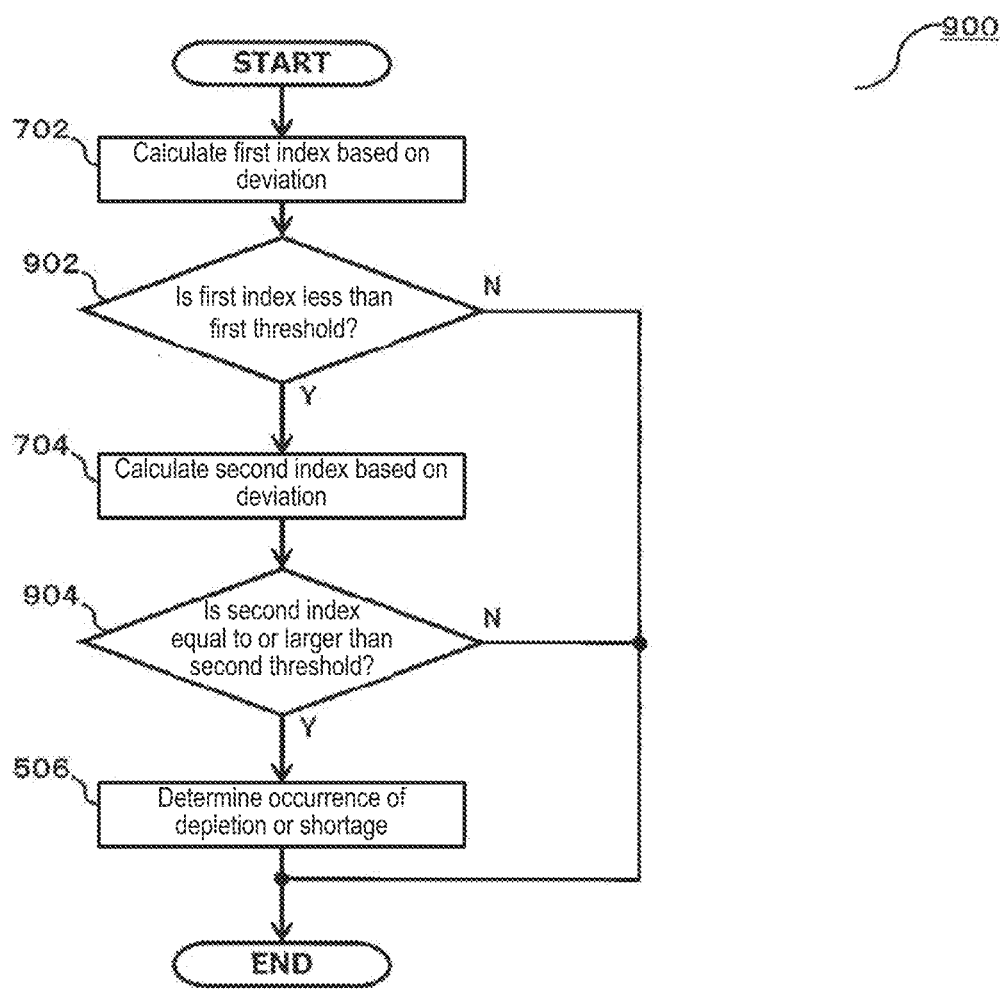
FIG. 9 is a flow chart of a third example process for performing determination on depletion or shortage of an aerosol source according to an embodiment of the present disclosure.

2-4 Third Example Process for Determining Occurrence of Depletion or Shortage of Aerosol Source FIG. 9 is a flow chart of a third example process 900 executed in step 318 or 324. Since some steps included in the example process 900 are the same as those included in the example process 500 or 700, steps that are not included in the example process 500 or 700 will be explained in the following description.

902 denotes a step of determining whether the first index is less than a first threshold value. The object of this step is to determine whether dispersion of data used for deriving the first index is small, i.e., whether the temperature of the load 132 is in a steady state. If the first index is less than the first threshold value, the process proceeds to step 704, and, if not, the process is terminated.

904 denotes a step of determining whether the second index is equal to or greater than a second threshold value. The object of this step is to determine whether dispersion of data used for deriving the second index is large. In this regard, the second threshold value may be the same as the first threshold value, or may be different from the first threshold value. If the second index is equal to or greater than the second threshold value, the process proceeds to step 506, and, if not, the process is terminated.

In this regard, in this example, it is supposed that each of the first index and the second index shows a value that becomes larger as the dispersion of the calculation data becomes larger. It should be reminded that, in the case that a first index and a second index, each showing a value that becomes smaller as the dispersion of the calculation data becomes larger, is used, step 902 may be configured to determine whether the first index is equal to or greater than the first threshold value, and step 904 may be configured to determine whether it is less than the threshold value.

In the following description, judgment of depletion or shortage of the aerosol source in the example process 900 will be explained with reference to FIG. 10.

Figure 10:
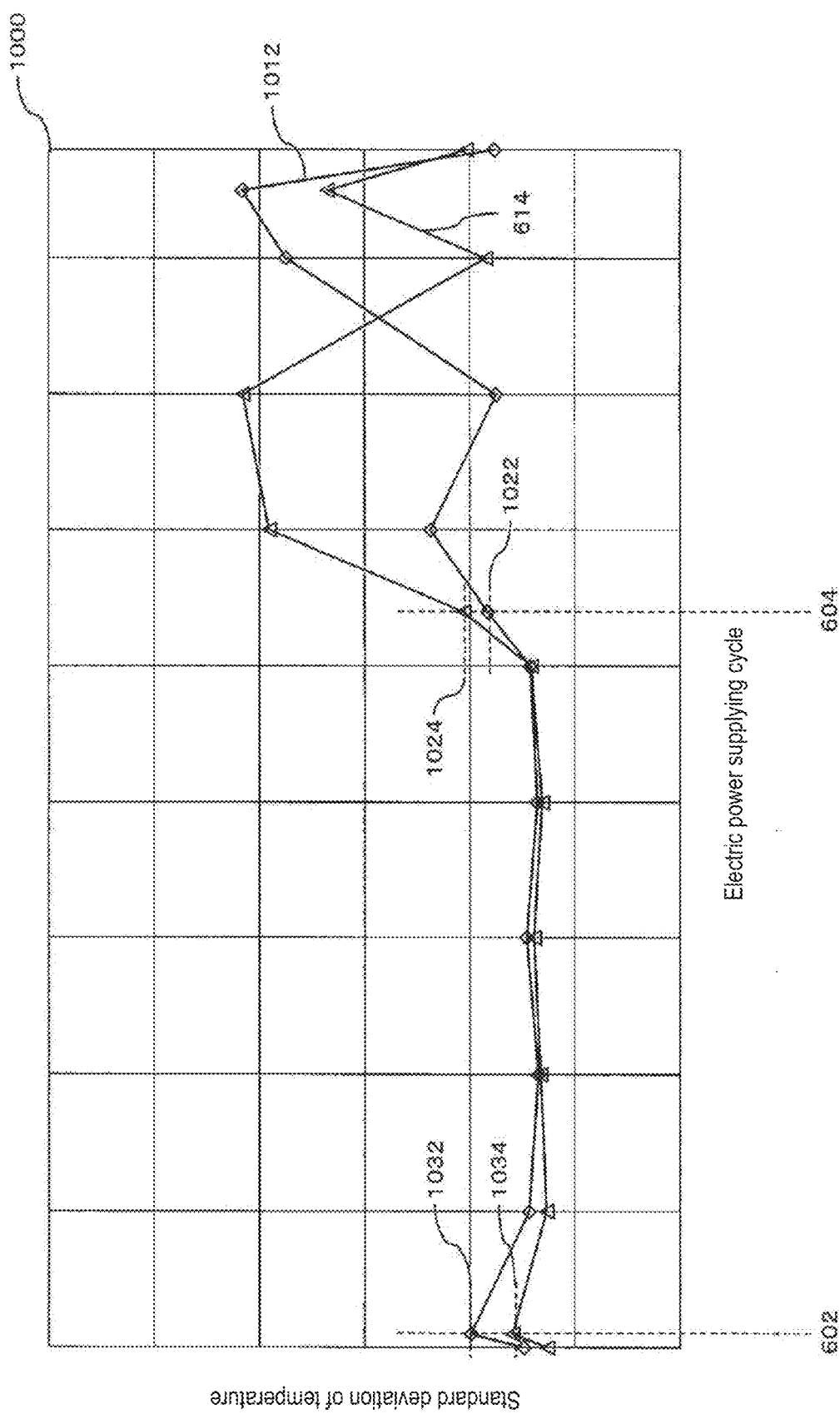
FIG. 10 is a graph in which standard deviations of temperature of a load relating to respective electric power supplying cycles are plotted.
Figure 11:
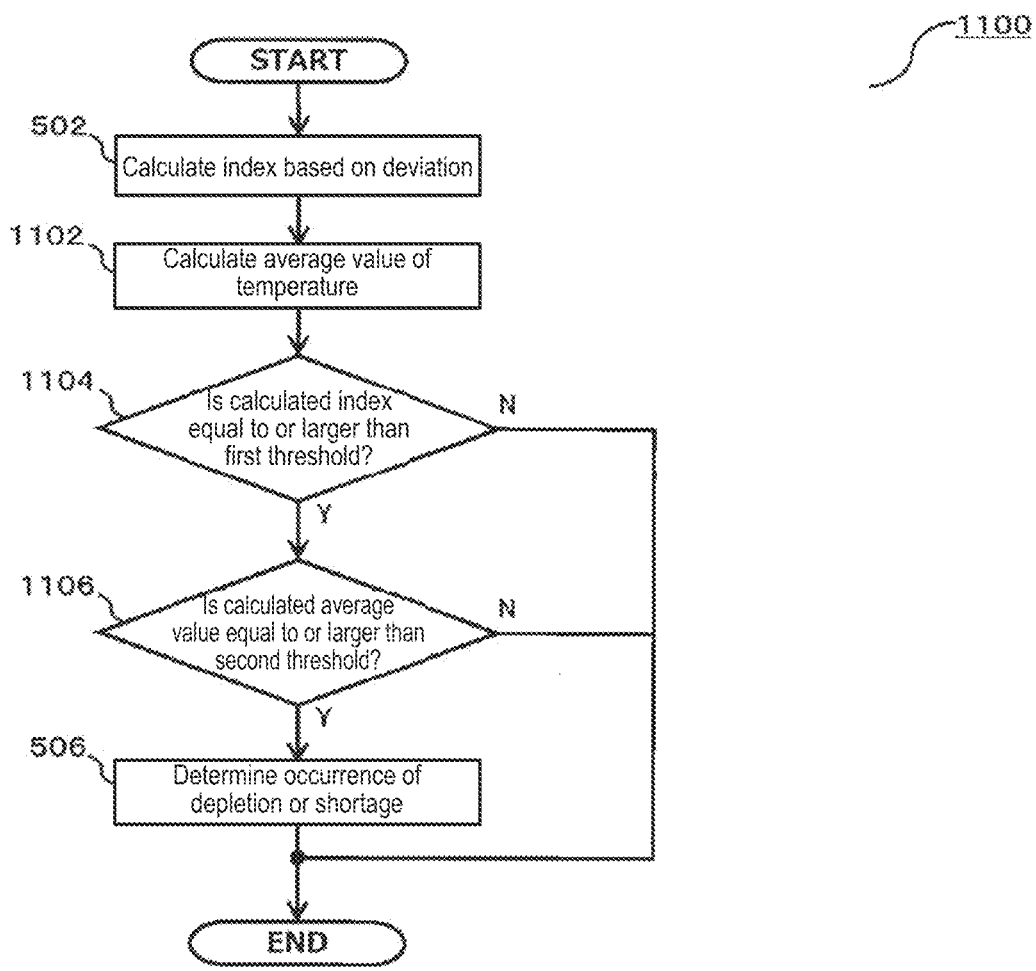
FIG. 11 is a flow chart of a fourth example process for performing determination on depletion or shortage of an aerosol source according to an embodiment of the present disclosure.

FIG. 10 is a graph 1000 in which standard deviations of the temperature of the load 132 derived from calculation data, that relate to respective electric power supplying cycles, are plotted, and the graph is similar to the graph 600. However, 1012 denotes a temperature profile derived from calculation data corresponding to a period, that is a first phase, from the time 435 to the time 436 (refer to FIG. 4B). In this regard, it is supposed in the explanation relating to the example process 900 that a second phase is a period from the time 436 to the time 437 (refer to FIG. 4B). Thus, the respective points in the standard deviation profiles 1012 and 614 correspond to the first indexes and the second indexes determined in steps 702 and 704, respectively.

Regarding the electric power supplying cycle 604, when the standard deviation profiles 1012 and 614 are compared with each other, it can be seen that the standard deviation 1022 in the former is smaller than the standard deviation 1024 in the latter. In other words, in an electric power supplying cycle at the time when the aerosol source in the storage unit or the like has been depleted or in short supply (an electric power supplying cycle at the time when the aerosol source in the holding unit or the like has been depleted), the dispersion in the first part of the temperature of the load 132 is small and the dispersion in the latter part is large. On the other hand, regarding the electric power supplying cycle 602, the standard deviation 1032 in the former is larger than the standard deviation 1034 in the latter. Regarding the above event, it is considered that, in the electric power supplying cycle 602, although the temperature increase in the load 132 is slow in an early stage of the temperature profile, the temperature of the load 132 enters a steady state at the boiling point or the like and stays therein in or after a middle stage of the temperature profile, so that, although dispersion in the first part of the temperature of the load 132 is large, dispersion in the latter part is small.

According to the example process 900, it becomes possible to reduce the risk to make an incorrect judgment, by using a second index that is derived from at least part of output values of the sensor after the output values of the sensor have come to a steady state, by using the above characteristic.

Regarding the judgment as to whether the output values of the sensor have come to a steady state, the judgment can be made by simply determining whether the output values of the sensor are in a predetermined range during a predetermined period of time, or whether a difference between an average value of the output values of the sensor during a predetermined period of time and a predetermined value is equal to or less than a predetermined value. Detailed explanation relating to the above matter is as follows: In the case that the remaining quantity of the aerosol source in the holding unit or the like is sufficient, the temperature of the load 132 converges at point near the boiling point or the like, presents a minor up-and-down motion microscopically, and enters a steady state. Also, although it will be explained later, the temperature of the load 132 enters a steady state, in the case that the remaining quantity of the aerosol source in the holding unit or the like is not sufficient and has not been depleted. Thus, in the case that the output of the sensor has entered a steady state, the output values of the sensor are maintained to be those in a predetermined range, and an average value thereof becomes that close to a predetermined value. Accordingly, the judgment in step 902 in the example process 900 may be that based on one of or both the output values and an average value of the output values of the sensor, and the above may be combined with the judgment based on the first index.

Further, the first index and the second index in steps 902 and 904 may be values between the standard deviation of the first part and the standard deviation of the latter part of the temperature of the load 132 in an electric power supplying cycle at the time when the aerosol source in the storage unit or the like has been depleted or in short supply (an electric power supplying cycle at the time when the aerosol source in the holding unit or the like has been depleted), for example, values between the standard deviation 1022 and the standard deviation 2014 in FIG. 10.

2-5 Fourth Example Process for Determining Occurrence of Depletion or Shortage of Aerosol Source FIG. 11 is a flow chart of a fourth example process 1100 executed in step 318 or 324. Since some steps included in the example process 1100 are the same as those included in the example process 500, steps that are not included in the example process 500 will be explained in the following description.

1102 denotes a step of calculating, based on calculation data, an average value of the temperature of the load 132.

1104 denotes a step similar to step 504. However, there are some differences such that the "threshold value" in step 504 is a "first threshold value" in step 1104, and, in the case that a calculated index is equal to or greater than the first threshold value, the process proceeds to step 1106. In this regard, in this example, it is supposed that the index shows a value that becomes larger as dispersion of calculation data becomes larger. It should be reminded that, in the case that an index showing a value that becomes smaller as the dispersion of the calculation data becomes larger is used, this step 902 may be configured to determine whether the index is less than the first threshold value.

1106 denotes a step of determining whether the average value calculated in step 1102 is equal to or greater than a second threshold value. If the calculated average value is equal to or greater than the second threshold value, the process proceeds to step 506, and, if not, the process is terminated.

In the following description, the judgment of depletion or shortage of the aerosol source in the example process 1100 will be explained with reference to FIG. 12.

Figure 12:
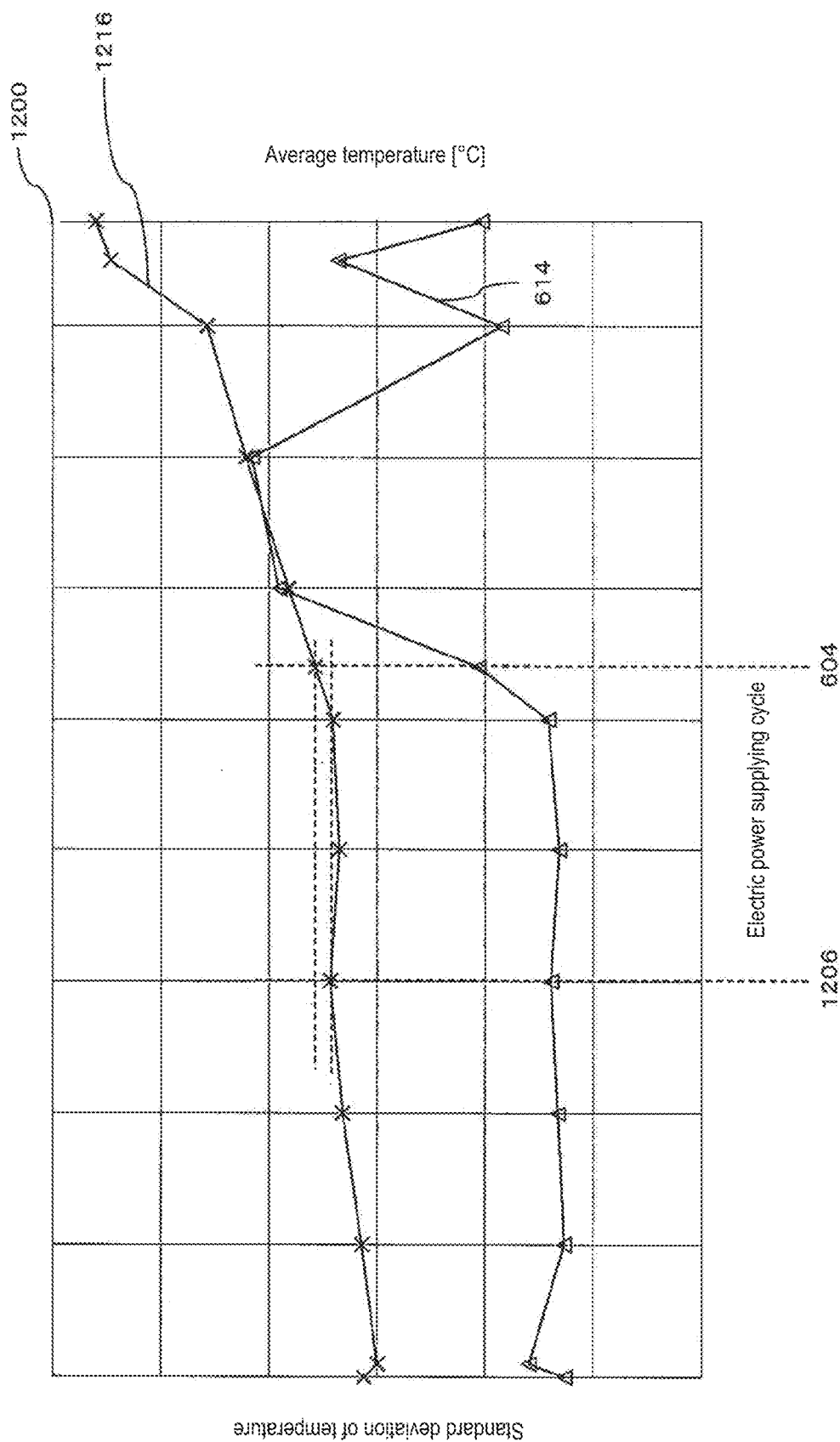
FIG. 12 is a graph in which standard deviations of temperature of and average temperature of a load relating to respective electric power supplying cycles are plotted.

FIG. 12 is a graph 1200 relating to respective electric power supplying cycles, in which standard deviations of the temperature of the load 132 and average temperature derived from calculation data, versus respective electric power supplying cycles, are plotted; and the graph is similar to the graph 600. However, 1216 denotes average temperature derived from calculation data corresponding to a period from the time 436 to the time 437 (refer to FIG. 4B). In the following description, the average temperature plotted in relation to respective electric power supplying cycles is referred to as an average temperature profile.

It is understood, as a result of study with respect to an average temperature profile 1216, that the average temperature in the electric power supplying cycle 604 is larger than the largest average temperature in an electric power supplying cycle in electric power supplying cycles before the above electric power supplying cycle, i.e., the average temperature in the electric power supplying cycle 1206. In other words, the average temperature in an electric power supplying cycle at the time when the aerosol source in the storage unit or the like is depleted or in short supply (an electric power supplying cycle during which the aerosol source in the holding unit or the like is depleted) is larger than the average temperature in an electric power supplying cycle at the time different from the above time. By additionally using average temperature when determining depletion or shortage of the aerosol source in the storage unit or the like, by using the above characteristic, it becomes possible to reduce the risk to make an incorrect judgment. In this regard, the second threshold value in step 1106 may be a value that is equal to or less than the average temperature in an electric power supplying cycle at the time when the aerosol source in the storage unit or the like is depleted or in short supply (an electric power supplying cycle during which the aerosol source in the holding unit or the like is depleted), and also is larger than the maximum average temperature at the time other than the above time.

In addition, regarding an event that the average temperature in an electric power supplying cycle at the time when the aerosol source in the storage unit or the like is depleted or in short supply (an electric power supplying cycle during which the aerosol source in the holding unit or the like is depleted) shows a relatively high value, explanation of the reason regarding why the event occurs may be that the solutions having lower boiling points in the mixed solutions forming the aerosol source are atomized preferentially, cooling effect on the load 132 provided by the aerosol source diminishes, and so on.

Figure 13:
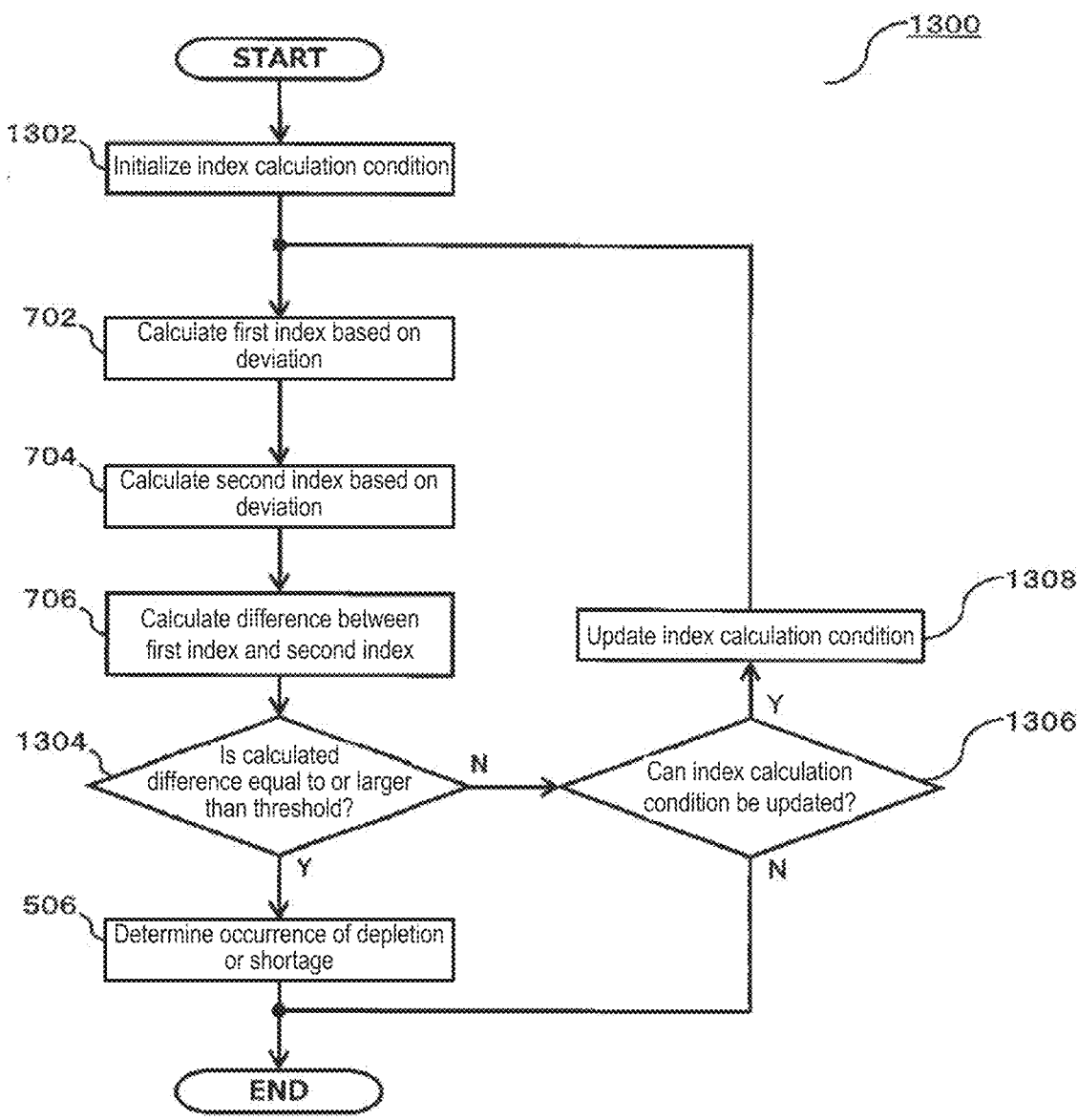
FIG. 13 is a flow chart of a fifth example process for performing determination on depletion or shortage of an aerosol source according to an embodiment of the present disclosure.

2-6 Fifth Example Process for Determining Occurrence of Depletion or Shortage of Aerosol Source FIG. 13 is a flow chart of a fifth example process 1300 executed in step 318 or 324. Since some steps included in the example process 1300 are the same as those included in the example processes 500 and 700, steps that are not included in the example processes 500 and 700 will be explained in the following description.

1302 denotes a step of initializing an index calculation condition. The index calculation condition is that designating data used for deriving a first index and a second index in step 702 and 704.

Figure 4C:
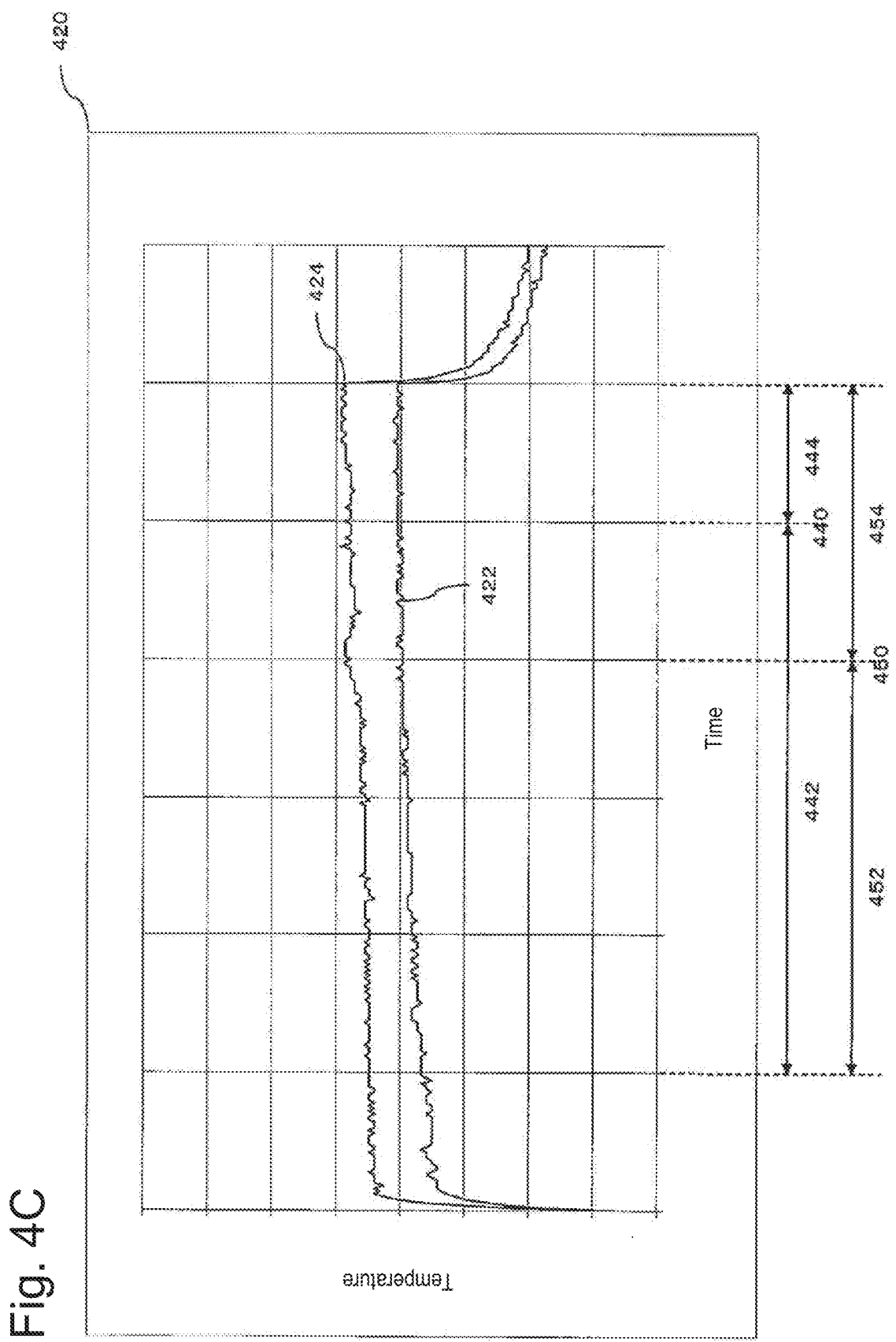
FIG. 4C is a graph in which temperature of a load in two electric power supplying cycles is plotted.

In the following description, initialization of the index calculation condition will be explained with reference to FIG. 4C. The graph shown in FIG. 4C is the same as that shown in FIG. 4B.

In the example process 1300, the calculation data can be divided into two parts by using a time as a reference (hereinafter, this will be referred to as a "dividing time"), and the first index can be derived from calculation data corresponding to a first part of the above calculation data, and the second index can be derived from calculation data corresponding to a latter part of the above calculation data. Thus, step 1302 can initialize the index calculation condition, for example, in such a manner that the first index is to be derived from calculation data corresponding to a first part (this may correspond to a first phase) 422 and the second index is to be derived from calculation data corresponding to a latter part (this may correspond to a second phase) 444, wherein the calculation data is divided based on the time 440. In this regard, it is preferable that the latter part 444 relating to the initialization be shorter. This is because, as will be explained later, it becomes easier to observe fluctuation of the temperature of the load 132 in or after a middle stage of a heating profile, that may occur only in an electric power supplying cycle during which the aerosol source in the holding unit or the like is depleted.

1304 denotes a step of determining whether the difference calculated in step 706 is equal to or greater than a threshold value. If the calculated difference is equal to or greater than the threshold value, the process proceeds to step 506, and, if not, the process proceeds to step 1306.

1306 denotes a step of determining whether the index calculation condition can be updated. If it is determined that the index calculation condition can be updated, the process proceeds to step 1308 for updating the index calculation condition, and, if not, the process is terminated.

In the following description, updating of the index calculation condition will be explained with reference to FIG. 4C.

Updating of the index calculation condition may be a process for shifting the dividing time to an earlier time. For example, by updating the dividing time to change it from the time 440 to the time 450, it is possible to derive the first index from calculation data corresponding to the first part 452 and the second index from calculation data corresponding to the latter part 454 in following steps 702 and 704. As a result, in the following steps 702 and 704, the first index is calculated from calculation data relating to an earlier time in a time series, and the second index is calculated from calculation data relating to a later time in the time series. The quantities of shifts of the dividing time relating to respective updates may be constant or different from each other.

In this regard, the judgment regarding whether the index calculation condition can be updated may be made by using any method such as that determining whether step 1308 has been performed a predetermined number of times, whether the dividing time has reached a predetermined time, whether the length of the first part has become a length equal to or less than a predetermined length, or the like.

The index based on the deviation changes according to part of calculation data used for calculating the index. As explained above, in an electric power supplying cycle during which the aerosol source in the holding unit or the like is depleted, there is a tendency for the temperature of the load 132 in or after a middle stage of a heating profile to fluctuate. If the index calculation condition is updated little by little, the temperature (samples) of the load 132 used for calculating the second index increases gradually. Accordingly, it becomes possible to determine whether depletion or shortage of the aerosol source has been occurring in the storage unit or the like, while focusing on fluctuation of the temperature of the load 132 in or after the middle stage. Thus, according to the example process 1300, it becomes possible to reduce the risk to make an incorrect judgment, by calculating an index based on deviation while changing calculation data.

3 Process for Inferring or Detecting State Relating to Aerosol Source

Figure 14:
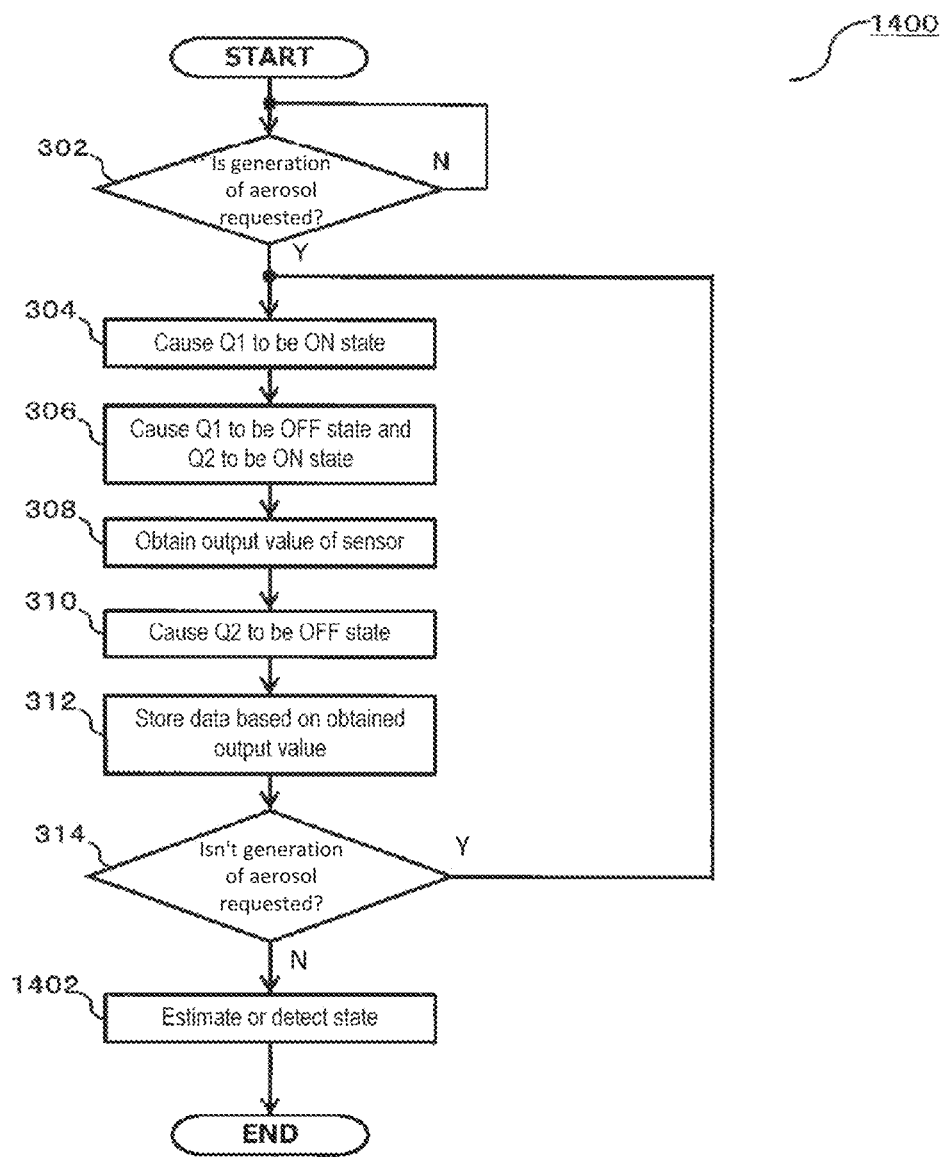
FIG. 14 is a flow chart of an example process for estimating or detecting a state relating to an aerosol source according to an embodiment of the present disclosure.

Regarding the process explained below, explanation thereof will be provided under the supposition that the control unit 106 executes all steps. However, it should be reminded that part of the steps may be executed by a different component in the aerosol generating device 100.
3-1 Outline of Process FIG. 14 is a flow chart of an example process 1400 for estimating or detecting a state of at least one of the storage unit 116A and the holding unit 130 according to an embodiment of the present disclosure. Since some steps included in the example process 1400 are the same as those included in the example process 300, steps that are not included in the example process 300 will be explained in the following description.

Figure 15:
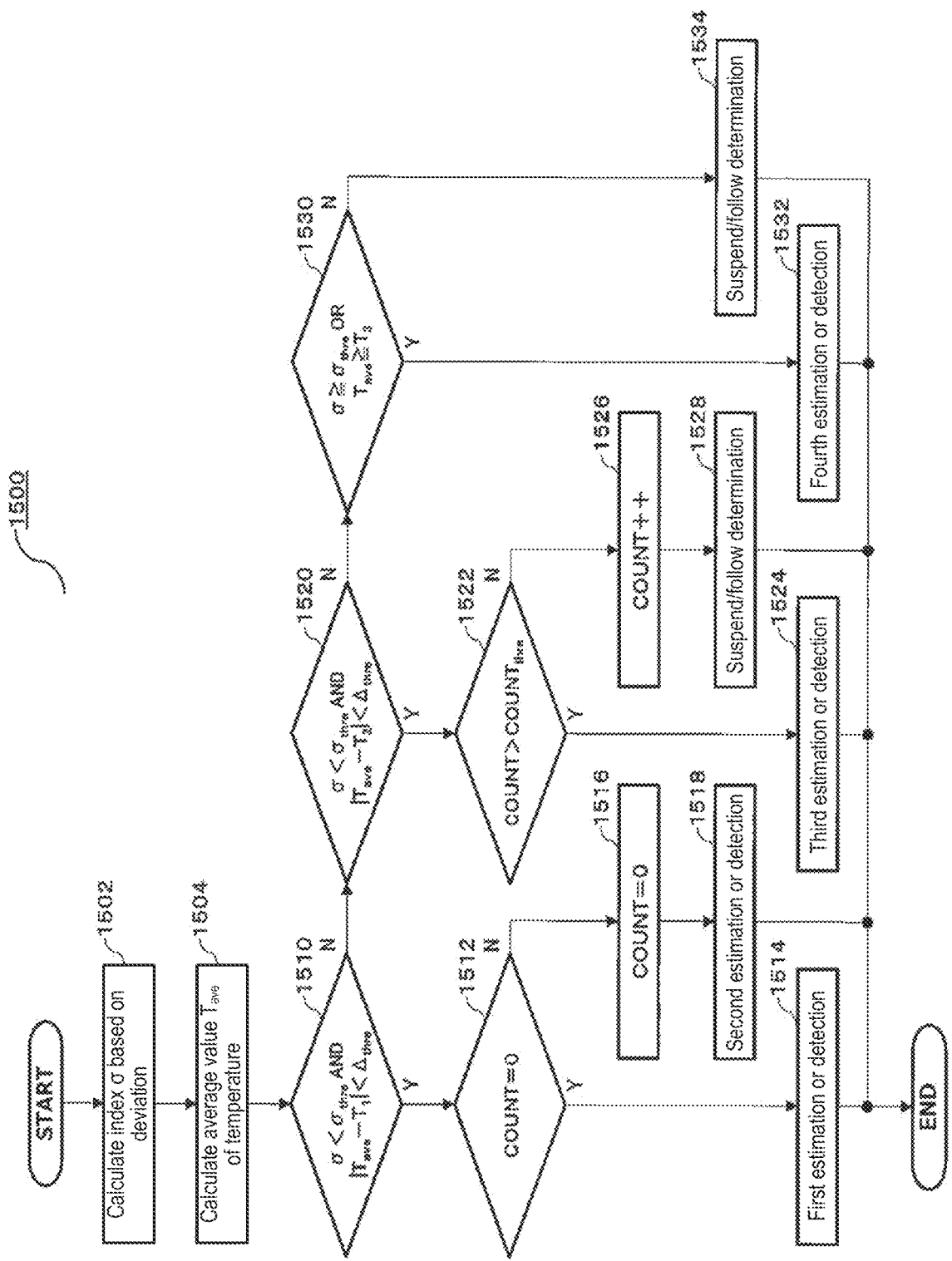
FIG. 15 is a flow chart of a first example process for estimating or detecting a state relating to an aerosol source according to an embodiment of the present disclosure.

1402 denotes a step of estimating or detecting the state of at least one of the storage unit 116A and the holding unit 130.
3-2 First Example Process for Inferring or Detecting State Relating to Aerosol Source FIG. 15 is a flow chart of a first example process 1500 executed in step 1402.

1502 denotes a step of calculating, based on the data stored in step 312, an index $\sigma$ based on deviation of output values of the sensor obtained in step 308.

In this regard, since the sensor in step 308 is that outputting values relating to the temperature of the load 132, the index $\sigma$ is an example of a value relating to behavior of the temperature of the load 132.

1504 denotes a step of calculating, based on the data stored in step 312, an average temperature $T_{ave}$ of the temperature of the load 132.

1510 denotes a step of determining whether the index $\sigma$ is smaller than a threshold value $\sigma_{thre}$, and whether the magnitude of the difference between the average temperature $T_{ave}$ and first predetermined temperature $T_1$ is less than a threshold value $\Delta_{thre}$.

Explanation regarding judgment as to whether the index $\sigma$ is smaller than the threshold value $\sigma_{thre}$ is as follows: The state that the index $\sigma$ is small implies that the dispersion of the output values of the sensor in step 308 is small, and, accordingly, the temperature of the load 132 is stable.

Figure 16:
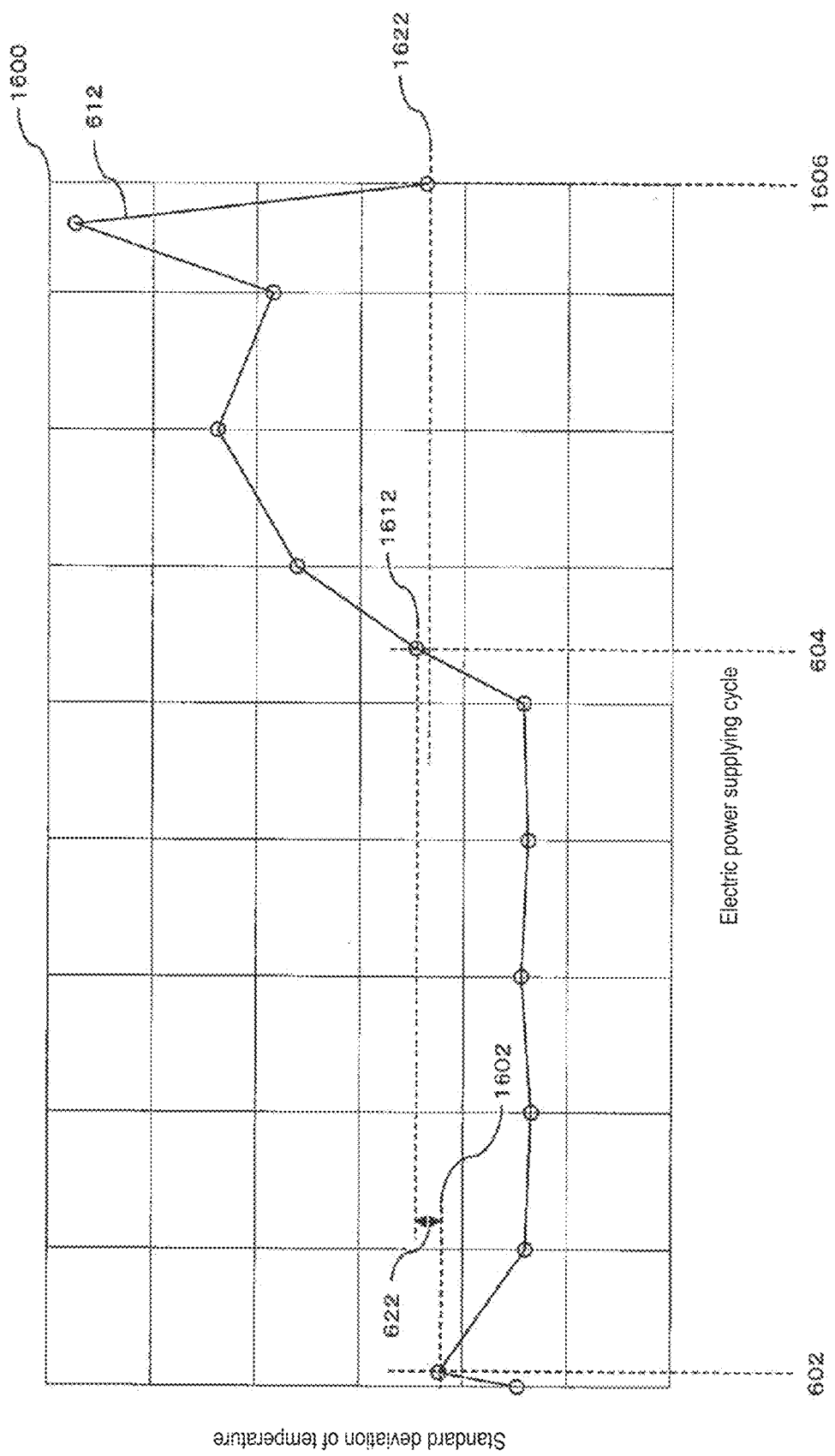
FIG. 16 is a graph in which standard deviations of temperature of a load relating to respective electric power supplying cycles are plotted.

In the following description, state that the dispersion of the output values of the sensor is small will be explained with reference to FIG. 16. FIG. 16 is a graph 1600 in which standard deviations of the temperature of the load 132 derived from calculation data, that relate to respective electric power supplying cycles, are plotted; and the graph is similar to the graph 600. According to the graph 1600, the standard deviation 1612 of the temperature in the electric power supplying cycle 604, that is the cycle at the time when first occurrence of a change of color in the load 132 due to a burnt deposit or oxidation has been visually confirmed, is larger than the maximum standard deviation in electric power supplying cycles at the time before the above time, i.e., the standard deviation 1602 in the electric power supplying cycle 602. Thus, if the threshold value $\sigma_{thre}$ is set to a value greater than the standard deviation 1602 and equal to or less than standard deviation 1612, the expression $\sigma<\sigma_{thre}$ becomes false in an electric power supplying cycle just before first occurrence of a change of color in the load 132 due to a burnt deposit or oxidation, so that the result of the judgment in step 1510 will be false.

FIG. 15 will be referred to again here; and, the temperature $T_1$ is that the temperature of the load 132 reaches when the remaining quantity of the aerosol source in the holding unit 130 sufficient, i.e., the boiling point of the aerosol source or the like. FIG. 4A will be referred to again here; and 411 denotes temperature such as the temperature $T_1$. For example, if the aerosol source is propylene glycol, the temperature $T_1$ may be 200 degrees Celsius. In this regard, the temperature $T_1$ may be determined by performing an experiment. In relation to the above matter, it has been known that, in the case that the remaining quantity of the aerosol source in the holding unit 130 is not sufficient, the whole energy supplied from the electric power source 110 is not completely used for atomizing the aerosol source, so that the average temperature $T_{ave}$ of the load 132 exceeds the temperature $T_1$.

That is, step 1510 is an example of the process for determining whether the temperature of the load 132 has been entered a steady state. Regarding the judgment as to whether the temperature of the load 132 has entered a steady state at certain temperature, the judgment can be made by simply determining whether the output values of the sensor are in a predetermined range, that corresponds to a predetermined range of temperature including the above certain temperature, during a predetermined period of time, or whether a difference between an average value of the output values of the sensor during a predetermined period of time and a predetermined value corresponding to the above certain temperature is equal to or less than a predetermined value.

If the index $\sigma$ is smaller than a threshold value $\sigma_{thre}$, and, also, the magnitude of the difference between the average temperature $T_{ave}$ and the first predetermined temperature $T_1$ is less than a threshold value $\Delta_{thre}$, the process proceeds to step 1512, and, if not, the process proceeds to step 1520.

1512 denotes a step of determining whether a variable COUNT is zero. As will be explained later, the variable COUNT is used as a flag for representing information relating to judgment made previously; to put it succinctly, the state that the variable COUNT is not zero represents the state that the result of judgment, that has been made in step 1510 in the past, does not represent true. In this regard, the variable COUNT may be initialized at any point in time before first execution of the example process 1400. Accordingly, at the time of first execution of the step 1512, the result of judgment necessarily represents true. If the variable COUNT is zero, the process proceeds to step 1514, and, if not, the process proceeds to step 1516.

1514 denotes a step of estimating or detecting a state that the remaining quantities of the aerosol sources in both the storage unit 116A and the holding unit 130 are sufficient. Here, estimation or detection in step 1514 will be explained with reference to FIG. 17.

1700 represents some patterns 1702-1710 of transitions of average temperature of the load 132 during electric power supplying cycles, in the case that the temperature of the load 132 has become stable. $C_1$ in each pattern represents a single electric power supplying cycle (hereinafter, this will be referred to as the "first electric power supplying cycle"), and $C_2$ represents a single electric power supplying cycle that occurs after the first electric power supplying cycle (hereinafter, this will be referred to as the "second electric power supplying cycle").

1702 represents a transition pattern, wherein the average temperature in the first electric power supplying cycle $C_1$ is close to the temperature $T_1$, and the average temperature in the second electric power supplying cycle $C_2$ is also close to the temperature $T_1$. In other words, the transition pattern 1702 shows an event that the temperature of the load 132 has been maintained in a steady state in the past and the present at temperature close to the temperature $T_1$, and the above event corresponds to the event that the remaining quantity of the aerosol source in the holding unit 130 has been sufficient in the past and the present.

Accordingly, when the transition pattern 1702 has appeared, it can be determined that the remaining quantity of the aerosol source in the holding unit 130 has been sufficient in the past and the present. When the above judgment is made, it is estimated that the remaining quantity of the aerosol source in the storage unit 116A is sufficient.

FIG. 15 will be referred to again here; and step 1514 is executed only when the variable COUNT is zero. Although it will be explained later, the variable COUNT increases when the temperature of the load 132 was not in a steady state at the boiling point of the aerosol source or the like in the past. In other words, an event that the process has proceeded to step 1514 implies that the temperature of the load 132 was in a steady state at the boiling point of the aerosol source or the like in the past, i.e., the transition pattern 1702 has appeared. Thus, in step 1514, it is possible to estimate or detect a state that the remaining quantities of the aerosol sources in both the storage unit 116A and the holding unit 130 are sufficient.

1516 denotes a step of initializing the variable COUNT to zero. The variable COUNT, that has been increased to have a large value as a result that the temperature of the load 132 was not in a steady state in the past at the boiling point of the aerosol source or the like, is initialized to zero in this step.

1518 denotes a step of estimating or detecting a state that the speed of atomization of the aerosol source in the holding unit 130 exceeds the speed of supply of the aerosol source from the storage unit 116A to the holding unit 130. Here, estimation or detection in step 1518 will be explained with reference to FIG. 17 again.

1706 represents a transition pattern, wherein the average temperature in the first electric power supplying cycle $C_1$ is close to the temperature $T_2$ that is higher than the temperature $T_1$, and, on the other hand, the average temperature in the second electric power supplying cycle $C_2$ is close to the temperature $T_1$. In other words, the transition pattern 1706 shows an event that, although the remaining quantity of the aerosol source in the holding unit 130 in the past was not sufficient, it is sufficient in the present. A transition pattern such as the transition pattern 1706 appears when imbalance between the speed of atomization of the aerosol source in the holding unit 130 and the speed of supply of the aerosol source from the storage unit 116A to the holding unit 130 has occurred. For example, in the case of an aerosol generating device 100 which adjusts electric power supplied from an electric power source 110 to a load 132 according to the speed of user's inhalation, it is assumed that there may be an event that the speed of inhalation is fast, and, accordingly, the speed of atomization of the aerosol source in the holding unit 130 exceeds the speed of supply of the aerosol source from the storage unit 116A to the holding unit 130. The above transition pattern 1706 would appear in the case that temporary shortage of the aerosol source in the holding unit 130 has occurred as a result of occurrence of the above assumed event, and the remaining quantity of the aerosol source in the holding unit 130 has recovered by supply of the aerosol source after temporary termination of the user's inhalation. It should be reminded that the transition pattern 1706 would also appear in the case that a period of time from an end of user's inhalation to a start of next user's inhalation is short.

FIG. 15 is referred to again; and step 1518 is that to which the process proceeds in the case that the variable COUNT is not zero although the temperature of the load 132 is in a steady state at the boiling point of the aerosol source or the like. The state that the variable COUNT is not zero means that the temperature of the load 132 has not been in a steady state in the past at the boiling point of the aerosol source of the like. That is, the event that the process has proceeded to step 1518 implies that the transition pattern 1706 has appeared. Thus, in step 1518, it is possible to estimate or detect a state that the speed of atomization of the aerosol source in the holding unit 130 has exceeded the speed of supply of the aerosol source from the storage unit 116A to the holding unit 130.

1520 denotes a step of determining whether the index σ is smaller than a threshold value $\sigma_{thre}$, and whether the magnitude of the difference between the average temperature $T_{ave}$ and the second predetermined temperature $T_2$ is less than a threshold value $\Delta_{thre}$. In this regard, the threshold value $\Delta_{thre}$ in step 1510 may be the same as or different from that in step 1520.

In the following description, the second predetermined temperature $T_2$ will be explained with reference to FIG. 4A again. The applicant has found that there is a case wherein the temperature of the load 132 enters a steady state at temperature 412 that is higher than the temperature 411, when the remaining quantity of the aerosol source in the holding unit 130 is not sufficient and has not been depleted. Although the cause of the above phenomenon has not yet investigated completely, it is considered that the cause may comprise complex factors. For example, it is considered that a cause of the above phenomenon may be partial depletion or shortage of the aerosol in the holding unit 130. Further, for example, it is considered that a cause of the above phenomenon may be change in the component of the aerosol source. Further, in the case that the aerosol source comprises a liquid mixture, it is considered that a cause of the above phenomenon may be differences between boiling points of solutions that are components of the aerosol (a solution having a lower boiling point is atomized more preferentially), for example. The temperature $T_2$ is the temperature 412 in the case explained above, and can be defined by performing an experiment.

That is, step 1520 is an example of a process for determining whether the temperature of the load 132 has entered a steady state at the above-explained temperature $T_2$.

If the index σ is smaller than a threshold value $σ_{thre}$, and the magnitude of the difference between the average temperature $T_{ave}$ and the second predetermined temperature $T_2$ is less than the threshold value $Δ_{thre}$, the process proceeds to step 1522, and, if not, the process proceeds to step 1530.

1522 denotes a step of determining whether the variable COUNT is equal to or greater than a threshold $COUNT_{thre}$. $COUNT_{thre}$ may be a predetermined value equal to or greater than 1. If the variable COUNT is equal to or greater than a threshold $COUNT_{thre}$, the process proceeds to step 1524, and, if not, the process proceeds to step 1526.

1524 denotes a step of estimating or detecting a state that the aerosol source in the holding unit 130 is short. In the following description, the judgment in step 1524 will be explained with reference to FIG. 17 again.

1708 represents a transition pattern, wherein the average temperature in the first electric power supplying cycle $C_1$ is close to the temperature $T_2$, and the average temperature in the second electric power supplying cycle $C_2$ is also close to the temperature $T_2$. In other words, the transition pattern 1708 shows an event that the temperature of the load 132 has been maintained in a steady state in the past and the present at temperature close to the temperature $T_2$. The above matter means that the remaining quantity of the aerosol source in the holding unit 130 has not been sufficient but has not been depleted, in the past and the present.

Accordingly, when the transition pattern 1708 has appeared, it can be determined that the remaining quantity of the aerosol source in the holding unit 130 has not been sufficient but has not been depleted in the past and the present, for example, has been short, in design. Further, when the transition pattern 1708 has appeared, there are the case that the remaining quantity of the aerosol source in the holding unit 130 has been short and the case that it has been depleted, in the past and the present; however, in design, it is possible to determine that depletion or shortage of the aerosol source in the storage unit 116A has occurred, without distinguish the above two cases.

Here, FIG. 15 will be referred to again; and step 1524 is executed only when the variable COUNT is equal to or greater than the threshold $COUNT_{thre}$; and, as will be explained later, the variable COUNT is incremented by 1 in step 1526. In other words, an event that the process has proceeded to step 1524 implies that judgment in step 1520 identifying that the temperature of the load 132 has entered a steady state at temperature T2 has been made at least the $COUNT_{thre}$ times, i.e., the temperature of the load 132 has been in a steady state at temperature near the temperature $T_2$ in the past and the present, and the transition pattern 1708 has appeared. Thus, in step 1524, it is possible to estimate or detect that the remaining quantity of the aerosol source in the holding unit 130 is short. Further, in step 1524, it is also possible to estimate or detect that the remaining quantity of the aerosol source in the storage unit 116A has been depleted or short. In this regard, in step 1524, without performing estimation or detection with respect to the holding unit 130 in the storing unit 116A and the holding unit 130, it is possible to estimate or detect that the remaining quantity of the aerosol source in the storage unit 116A has been depleted or short.

Further, it is possible to obtain, by performing an experiment, the number of electric power supplying cycles in a period from the time when the process has reached step 1524 for the first time to the time when the aerosol source in the holding unit 130 is actually depleted, and set the predetermined number of times to the obtained number of electric power supplying cycles. In step 1524, it is possible to estimate or detect that the remaining quantity of the aerosol source in the holding unit 130 is depleted, after a user of the aerosol generating device 100A performs the predetermined number of times of puffs, i.e., after the predetermined number of times of electric power supplying cycles occur. In other words, the transition patter 1708 shows a symptom of depletion of the aerosol source in the holding unit 130. Further, it can be configured in such a manner that, in the case that step 1524 is executed, supply of electric power to the load 132 is suppressed after the predetermined number of times, or the number of times less than the predetermined number of times, of electric power supplying cycles has occurred. If the above configuration is adopted, supply of electric power to the load 130 can be avoided, in a state that a sufficient quantity of aerosol cannot be generated, or a state that aerosol having intended fragrance inhaling taste cannot be generated. In other words, the temperature of the load 132 does not become high, since supply of electric power to the load 130 can be avoided in the state that the remaining quantity of the aerosol source in the holding unit 130 has been depleted.

1526 denotes a step of incrementing the variable COUNT. The variable COUNT can be incremented by 1 by the above step.

1528 denotes a step of making a judgment for specifying whether determining with respect to the state relating to the aerosol source should be suspended, or the determining should follow the most recent judgment. In the following description, the judgment in step 1528 will be explained with reference to FIG. 17 again.

1704 represents a transition pattern, wherein the average temperature in the first electric power supplying cycle $C_1$ is close to the temperature $T_1$, and, on the other hand, the average temperature in the second electric power supplying cycle $C_2$ is close to the temperature $T_2$. With respect to the above case, if the second electric power supplying cycle $C_2$ is assumed to be a first electric power supplying cycle (hereinafter, this may also be referred to as an assumed first electric power supplying cycle), and if an electric power supplying cycle after the assumed first electric power supplying cycle is assumed to be a second electric power supplying cycle (hereinafter, this may also be referred to as an assumed second electric power supplying cycle), it is considered that the transition pattern 1706 has appeared substantially if the average temperature of the load 132 has decreased to the temperature $T_1$ and that the transition pattern 1708 has appeared substantially if the average temperature of the load 132 is the temperature $T_2$, in the assumed second electric power supplying cycle. In other words, in the case that the transition pattern 1704 has appeared, it is difficult to distinguish, i.e., determine whether judgment identifying that imbalance between the speed of atomization of the aerosol source in the holding unit 130 and the speed of supply of the aerosol source from the storage unit 116A to the holding unit 130 has occurred, like that in the case of the transition pattern 1706, should be made, or judgment identifying that the remaining quantity of the aerosol in the storage unit 116A is short, like that in the case of the transition pattern 1708, should be made. Thus, in the case that the transition pattern 1704 has appeared, it is possible to make a judgment deciding that determining is to be suspended, or a judgment deciding to follow result of a previous judgment (this includes a judgment deciding that determining is to be suspended, or a judgment deciding to follow result of a previous judgment).

FIG. 15 will be referred to again; and step 1528 is executed only when the variable COUNT is equal to or less than the threshold $COUNT_{thre}$. In this regard, the judgment in step 1524 is made in the case that the variable COUNT has become a value larger than the threshold $COUNT_{thre}$, and the judgment in step 1524 is made in the case that the temperature of the load 132 has decreased to temperature near the first predetermined temperature $T_1$ before the variable COUNT becomes a value larger than the threshold $COUNT_{thre}$. In other words, when the process has proceeded to step 1528, it can be regarded that the transition patter 1704 has appeared. Thus, in step 1528, it is possible to make a judgment deciding that determining is to be suspended, or a judgment deciding to follow result of a previous judgment.

1530 denotes a step of determining whether the index σ is equal to or greater than the threshold $σ_{thre}$, or whether the average temperature $T_{ave}$ is equal to or greater than a third predetermined temperature. When FIG. 17 is referred to again, $T_3$ represents the third predetermined temperature. The temperature $T_3$ may be temperature that is larger than the temperature $T_2$, and smaller than the maximum temperature that the temperature of the load 132 reaches when the aerosol source in the holding unit 130 has been depleted, and the temperature $T_3$ may be determined by performing an experiment. For example, the temperature $T_2$ may be 350 degrees Celsius.

1532 denotes a step of estimating or detecting a state that the remaining quantity of the aerosol source in the holding unit 130 has been depleted.

Step 1532 is executed when the index σ is equal to or greater than the threshold $σ_{thre}$. When FIG. 16 is referred to again, the index σ increases in principle, when the number of times of supply of electric power exceeds a predetermined number of times. Especially, as explained above, if the threshold $σ_{thre}$ is set to a value greater than the standard deviation 1602 and equal to or less than the standard deviation 1612, it is possible to determine whether the state of the remaining quantity of the aerosol source in the holding unit 130 is in a state just before first occurrence of a change of color in the load 132 due to a burnt deposit or oxidation. In this regard, an event that a change of color in the load 132 due to a burnt deposit or oxidation has occurred can be regarded as an event that the remaining quantity of the aerosol source in the holding unit 130 has been depleted; thus, in design, in the case that the index σ is equal to or greater than the threshold $σ_{thre}$, it is possible to estimate or detect a state that the remaining quantity of the aerosol source in the holding unit 130 has been depleted.

Further, step 1532 is executed when the average temperature $T_{ave}$ is equal to or greater than the temperature $T_3$. When FIG. 16 is referred to again, there is a tendency that the standard deviation 1612 of the temperature in the electric power supplying cycle 604 is smaller than a standard deviation of temperature in an electric power supplying cycle after the electric power supplying cycle 604. However, the standard deviation 1622 of the temperature in the electric power supplying cycle 1606 is smaller than the standard deviation 1612 of the temperature in the electric power supplying cycle 604. It is considered that the above event has occurred as a result that the heating effect due to supply of electric power from the electric power source 110 to the load 132 and the cooling effect due to the air around the load 132 are balanced as a result of complete depletion of the aerosol source, and the temperature of the load 132 has entered a steady state at relatively high temperature.

Figure 17:
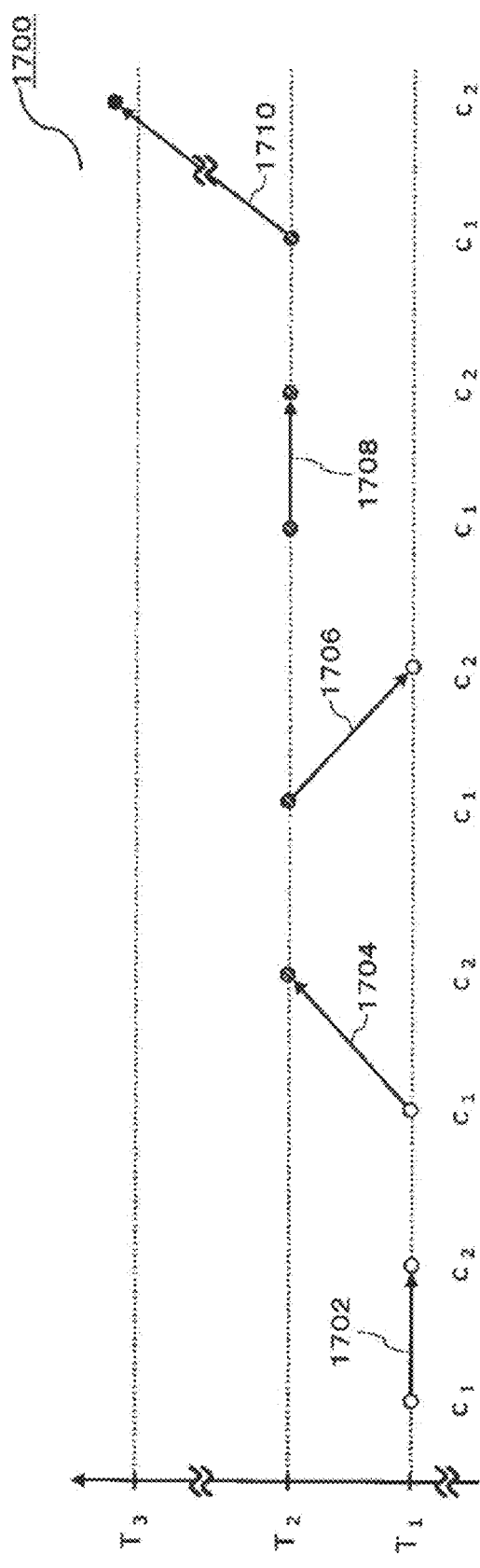
FIG. 17 represents some patterns regarding transition of average temperature between electric power supplying cycles.

Incidentally, it can be estimated that, in the electric power supplying cycle 1606, since a period of time has elapsed since the electric power supplying cycle 604, the temperature of the load 132 has reached to a temperature close to the maximum temperature that the temperature of the load 132 can reach when the aerosol source in the holding unit 130 has been depleted. Thus, even in the case that the average temperature $T_{ave}$ is equal to or greater than the temperature $T_3$, it is possible to estimate or detect a state that the remaining quantity of the aerosol source in the holding unit 130 has been depleted. Here, FIG. 17 is referred to, and it should be reminded that, in the case that the average temperature of the load 132 in the past is close to the temperature $T_2$, it is considered that the transition pattern 1710 has appeared when it is determined that the average temperature $T_{ave}$ is equal to or greater than the temperature $T_3$.

The case that the aerosol source in the holding unit 130 has been depleted implies that the aerosol source is not supplied from the storage unit 116A to the holding unit 130, that is, the remaining quantity of the aerosol source in the storage unit 115A has been depleted or short. Thus, in step 1532, it is possible to estimate or detect the state that the remaining quantity of the aerosol source in the storage unit 115A has been depleted or short, and the state that the remaining quantity of the aerosol source in the holding unit 130 has been depleted.

If it is determined that the index σ is equal to or greater than the threshold value $σ_{thre}$, or the average temperature $T_{ave}$ is equal to or greater than the third predetermined temperature $T_3$, the process proceeds to step 1532, and, if not, the process proceeds to step 1534.

1534 denotes a step to which the process proceeds if result of judgment in each of steps 1510, 1520, and 1530 shows false, and the step may be a step of making a judgment, similar to that in step 1528, for specifying whether determining with respect to the state relating to the aerosol source should be suspended or the determining should follow the most recent judgment.

Figure 18:
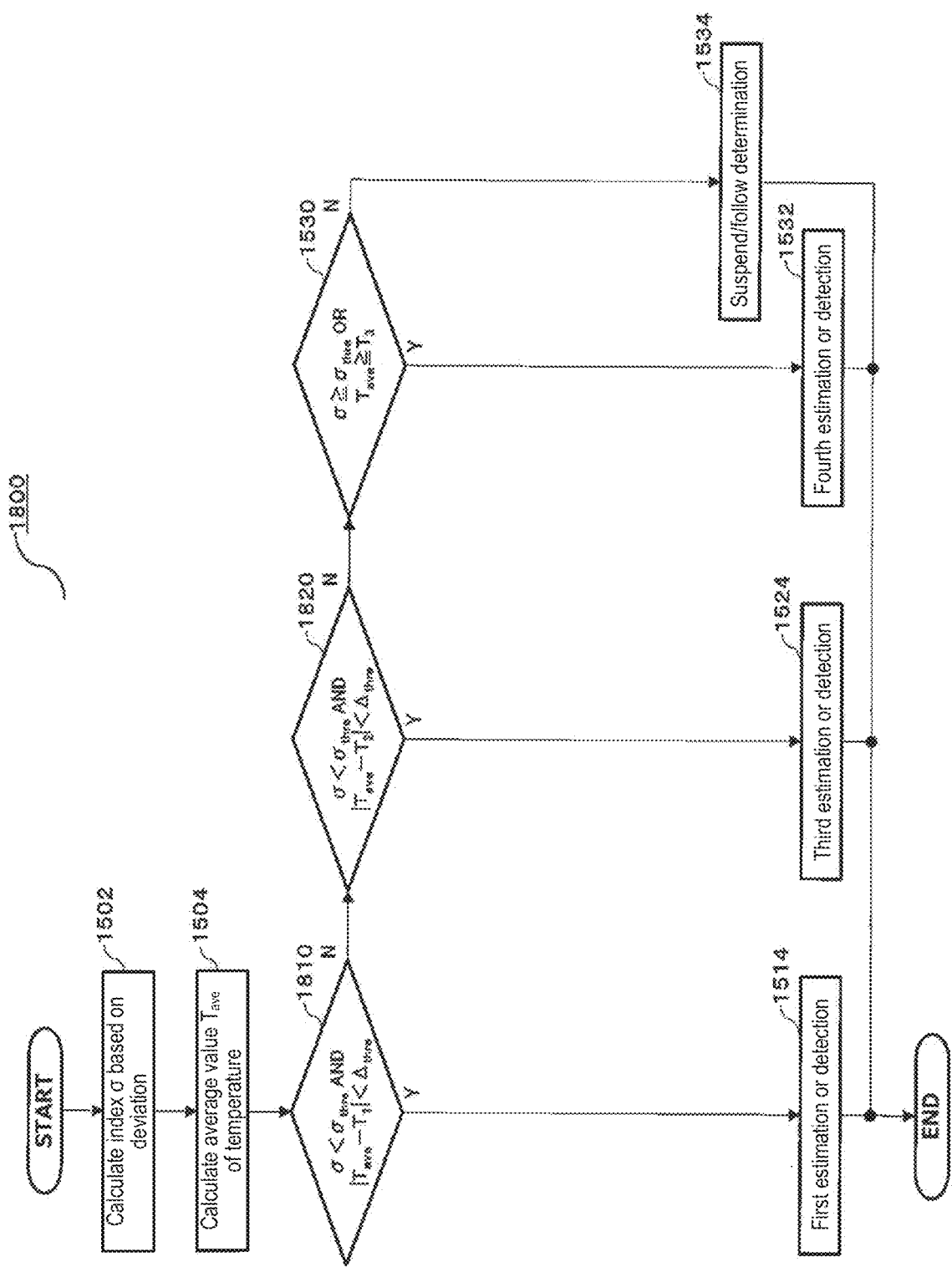
FIG. 18 is a flow chart of a second example process for estimating or detecting a state relating to an aerosol source according to an embodiment of the present disclosure.

3-3 Second Example Process for Inferring or Detecting State Relating to Aerosol Source FIG. 18 is a flow chart of a second example process 1800 executed in step 1402. Since some steps included in the example process 1800 are the same as or similar to those included in example step 1800, steps that are not included in the example process 1800 will be explained in the following description.

1810 is a step similar to step 1510, and the only difference between them is the point that, if the index σ is less than the threshold value $σ_{thre}$, and the magnitude of a difference between the average temperature $T_{ave}$ and the first predetermined temperature $T_1$ is less than the threshold value $Δ_{thre}$, the process proceeds to step 1514, and, if not, the process proceeds to step 1820. That is, according to the example process 1800, when it is determined that the temperature of the load 132 has been in a steady state at the boiling temperature of the aerosol source or the like $T_1$, it is possible to immediately estimate or detect the state that the remaining quantities of aerosol sources in both the storage unit 116A and the holding unit 130 are sufficient.

1820 is a step similar to step 1520, and the only difference between them is the point that, if the index σ is less than the threshold value $σ_{thre}$, and the magnitude of a difference between the average temperature $T_{ave}$ and the second predetermined temperature $T_2$ is less than the threshold value $Δ_{thre}$, the process proceeds to step 1524. That is, according to the example process 1800, when it is determined that the temperature of the load 132 has been in a steady state at the temperature $T_2$, it is possible to immediately estimate or detect the state that at least the remaining quantity of the aerosol source in the holding unit 130 is short.

When the example process 1500 and the example process 1800 are compared with each other, there is a difference that the variable COUNT is used in the former although the variable COUNT is not used in the latter. Further, there is a difference that the first to fourth estimation or detection can be performed in the former, although the second estimation or detection cannot be performed in the former. In the example process 1500 which uses the variable COUNT, although it takes time to estimate or detect a state of at least one of the storage unit 116A and the holding unit 130, precision of estimation and detection is guaranteed. On the other hand, in the example process 1800, although it is possible to estimate or detect a state of at least one of the storage unit 116A and the holding unit 130 in a simple manner, precision thereof is lower than that of the example process 1500.

4. Concluding Remarks

In the above description, the embodiments of the present disclosure have been explained as aerosol generating devices and methods for operating the aerosol generating devices. However, it will be understood that the present disclosure may be implemented as programs for making a processor execute the methods when the programs are executed by the processor, or a computer-readable storage medium storing the above programs.

In the above description, although the embodiments of the present disclosure have been explained, it should be understood that the embodiments are mere examples and are not those for limiting the scope of the present disclosure. It should be understood that change, addition, modification, and so on of each of the embodiments can be made appropriately, without departing the gist and the scope of the present disclosure. The scope of the present disclosure should not be limited by any of the above-explained embodiments, and should be defined by the claims and equivalents thereof only.

REFERENCE SIGNS LIST

110A, 110B . . . Aerosol generating device; 102 . . . Main body; 104A . . . Cartridge; 104B . . . Aerosol generating article; 106 . . . Control unit; 108 . . . Notification unit; 110 . . . Electric power source; 112A-112D . . . Sensor; 114 . . . Memory; 116A . . . Storage unit; 116B . . . Aerosol base material; 118A, 118B . . . Atomization unit; 120 . . . Air taking-in flow path; 121 . . . Aerosol flow path; 122 . . . Suction opening; 130 . . . Holding unit; 132 . . . Load; 134 . . . Circuit; 202 . . . First circuit; 204 . . . Second circuit; 206, 210, 214 . . . FET; 208 . . . Conversion unit; 212 . . . Resistance; 216 . . . Diode; 218 . . . Inductor; 220 . . . Capacitor; 402 . . . Warming period; 404 . . . Cooling period; 411 . . . Temperature $T_1$; 412 . . . Temperature $T_2$; 422, 424 . . . Temperature profile of load; 432, 442, 452 . . . First phase; 434, 444, 454 . . . Second phase; 440, 450 . . . Dividing time; 612, 614, 814 . . . Standard deviation profile of temperature of load; 1216 . . . Average temperature profile of load; 1702, 1704, 1706, 1708, 1710 . . . Transition pattern

The invention claimed is:

1. An aerosol generating device comprising:
a storage configured to store an aerosol source;
a load configured to atomize the aerosol source by heat generated by receiving supply of electric power from an electric power source;
a fibrous or porous material configured to retain the aerosol source, which is supplied from the storage, in a state that the aerosol source can be heated by the load;
a sensor configured to output a value relating to temperature of the load; and
circuitry configured to:
perform, in response to detecting a predetermined input from a user corresponding to a request for generation of aerosol, electric power supplying cycles by supplying electric power from the electric power source to the load; and
estimate or detect at least one of a state of the storage and a state of the fibrous or porous material based at least on first values and second values, wherein
the first values are:
output values of the sensor obtained in a first electric power supplying cycle, or
values relating to behavior of the temperature of the load in the first electric power supplying cycle, the values derived from the output values obtained in the first electric power supplying cycle;
the first electric power supplying cycle is a single one of the electric power supplying cycles;
the second values are:
output values of the sensor obtained in a second electric power supplying cycle, or
values relating to behavior of the temperature of the load in the second electric power supplying cycle, the values derived from the output values obtained in the second electric power supplying cycle; and
the second electric power supplying cycle is a single one of the electric power supplying cycles occurring after the first electric power supplying cycle.

2. The aerosol generating device of claim 1, wherein the circuitry is configured to:
estimate or detect, in case that at least one the first values and the second values represent that the temperature of the load has reached a steady state at second temperature that is higher than first temperature at which aerosol is generated from the fibrous or porous material in a saturation state of the aerosol source, at least one of:
a remaining quantity of the aerosol source in the storage,
a remaining quantity of the aerosol source in the fibrous or porous material, and
relationship between speed of atomization of the aerosol source in the fibrous or porous material and speed of supply of the aerosol source from the storage to the fibrous or porous material receptacle.

3. The aerosol generating device of claim 2, wherein the circuitry is configured to:
estimate or detect, in a case that the first values represent that the temperature of the load has reached a steady state at the second temperature, at least one of:
shortage or depletion of a remaining quantity of the aerosol source in the storage, and
that speed of atomization of the aerosol source in the fibrous or porous material is faster than speed of supply of the aerosol source from the storage to the fibrous or porous material.

4. The aerosol generating device of claim 3, wherein circuitry is configured to:
estimate or detect, in a case that the first values represent that the temperature of the load has reached a steady state at the second temperature, and that the second values represent that the temperature of the load has reached a steady state at the second temperature, shortage or depletion of a remaining quantity of the aerosol source in the storage.

5. The aerosol generating device of claim 3, wherein the circuitry is configured to:
estimate or detect, in a case that the first values represent that the temperature of the load has reached a steady state at the second temperature, and that the second values represent that the temperature of the load has reached a steady state at the first temperature, that speed of atomization of the aerosol source in the fibrous or porous material is faster than speed of supply of the aerosol source from the storage to the fibrous or porous material.

6. The aerosol generating device of claim 2, wherein the circuitry is configured to estimate or detect, in a case that the second values represent that the temperature of the load has reached a steady state at the second temperature, that shortage or depletion of a remaining quantity of the aerosol source in the storage has been occurring.

7. The aerosol generating device of claim 2, wherein the circuitry is configured to estimate or detect, in a case that the first values represent that the temperature of the load has reached a steady state at the second temperature, and that at least one of an average value of the second value and a value derived based on deviation of the second value is greater than a threshold value:
that shortage or depletion of a remaining quantity of the aerosol source in the storage has been occurring, and
that depletion of a remaining quantity of the aerosol source in the fibrous or porous material has been occurring.

8. The aerosol generating device of claim 2, wherein the circuitry is configured to determine, based on at least one of:
continuous output values of the sensor in the first electric power supplying cycle or the second electric power supplying cycle,
an average value of the output values in the first electric power supplying cycle or the second electric power supplying cycle, and
a value derived based on deviation of the output values in the first electric power supplying cycle or the second electric power supplying cycle,
that the first values or the second values represent that the temperature of the load has reached a steady state.

9. The aerosol generating device of claim 1, wherein the circuitry is configured to estimate or detect, in a case that the second values represent that the temperature of the load has reached a steady state at temperature higher than temperature at which aerosol is generated from the fibrous or porous material in a saturation state of the aerosol source, that a remaining quantity of the aerosol source in the fibrous or porous material will be depleted after completion of a predetermined number of times of the electric power supplying cycles.

10. The aerosol generating device of claim 1, wherein the circuitry is configured to estimate or detect, in a case that both the first values and the second values represent that the temperature of the load has reached a steady state at temperature higher than temperature at which aerosol is generated from the aerosol source, that a remaining quantity of the aerosol source in the fibrous or porous material will be depleted after completion of a predetermined number of times of the electric power supplying cycles.

11. A method for operating an aerosol generating device, wherein the aerosol generating device comprises: a storage configured to store an aerosol source; a load configured to atomize the aerosol source by heat generated by receiving supply of electric power from an electric power source; a fibrous or porous material configured to retain the aerosol source, which is supplied from the storage, in a state that the aerosol source can be heated by the load; a sensor configured to output a value relating to temperature of the load; and circuitry, wherein the method comprises, by the circuitry:
performing, in response to detecting a predetermined input from a user corresponding to a request for generation of aerosol, electric power supplying cycles by supplying electric power from the electric power source to the load; and
estimating or detecting at least one of a state of the storage and a state of the fibrous or porous material based at least on first values and second values, wherein
the first values are:
output values of the sensor obtained in a first electric power supplying cycle, or
values relating to behavior of the temperature of the load in the first electric power supplying cycle, the values derived from the output values obtained in the first electric power supplying cycle;
the first electric power supplying cycle is a single one of the electric power supplying cycles;
the second values are:
output values of the sensor obtained in a second electric power supplying cycle, or
values relating to behavior of the temperature of the load in the second electric power supplying cycle, the values derived from the output values obtained in the second electric power supplying cycle; and
the second electric power supplying cycle is a single one of the electric power supplying cycles occurring after the first electric power supplying cycle.

12. A non-transitory computer readable storage medium storing a program causing the circuitry to perform the method of claim 11, when the program is executed by the circuitry.

13. The method of claim 11, further comprising:
estimating or detecting, in case that at least one the first values and the second values represent that the temperature of the load has reached a steady state at second temperature that is higher than first temperature at which aerosol is generated from the fibrous or porous material fibrous or porous material in a saturation state of the aerosol source, at least one of:
a remaining quantity of the aerosol source in the storage,
a remaining quantity of the aerosol source in the fibrous or porous material, and
relationship between speed of atomization of the aerosol source in the fibrous or porous material and speed of supply of the aerosol source from the storage to the fibrous or porous material.

14. The method of claim 13, further comprising:
estimating or detecting, in a case that the second values represent that the temperature of the load has reached a steady state at the second temperature, that shortage or depletion of a remaining quantity of the aerosol source in the storage has been occurring.

15. The method of claim 13, further comprising:
estimating or detecting, in a case that the first values represent that the temperature of the load has reached a steady state at the second temperature, and that at least one of an average value of the second value and a value derived based on deviation of the second value is greater than a threshold value:

that shortage or depletion of a remaining quantity of the aerosol source in the storage has been occurring, and
that depletion of a remaining quantity of the aerosol source in the fibrous or porous material has been occurring.

16. The method of claim 13, further comprising:
estimating or detecting, in a case that the first values represent that the temperature of the load has reached a steady state at the second temperature, at least one of:
shortage or depletion of a remaining quantity of the aerosol source in the storage, and
that speed of atomization of the aerosol source in the fibrous or porous material is faster than speed of supply of the aerosol source from the storage to the fibrous or porous material.

17. The method of claim 16, further comprising:
estimating or detecting, in a case that the first values represent that the temperature of the load has reached a steady state at the second temperature, and that the second values represent that the temperature of the load has reached a steady state at the second temperature, shortage or depletion of a remaining quantity of the aerosol source in the storage.

18. The method of claim 16, further comprising:
estimating or detecting, in a case that the first values represent that the temperature of the load has reached a steady state at the second temperature, and that the second values represent that the temperature of the load has reached a steady state at the first temperature, that speed of atomization of the aerosol source in the fibrous or porous material is faster than speed of supply of the aerosol source from the storage to the fibrous or porous material.

19. The method of claim 11, further comprising:
estimating or detecting, in a case that the second values represent that the temperature of the load has reached a steady state at temperature higher than temperature at which aerosol is generated from the fibrous or porous material in a saturation state of the aerosol source, that a remaining quantity of the aerosol source in the fibrous or porous material will be depleted after completion of a predetermined number of times of the electric power supplying cycles.

20. The method of claim 11, further comprising:
estimating or detecting, in a case that both the first values and the second values represent that the temperature of the load has reached a steady state at temperature higher than temperature at which aerosol is generated from the aerosol source, that a remaining quantity of the aerosol source in the fibrous or porous material will be depleted after completion of a predetermined number of times of the electric power supplying cycles.

* * * * *